US012649752B2

(12) United States Patent
Sato et al.

(10) Patent No.: US 12,649,752 B2
(45) Date of Patent: Jun. 9, 2026

(54) ZIRCONIUM-89 OXINE COMPLEX AS A CELL LABELING AGENT FOR POSITRON EMISSION TOMOGRAPHY

(71) Applicant: The United States of America, as represented by the Secretary, Department of Health and Human Services, Bethesda, MD (US)

(72) Inventors: Noriko Sato, Potomac, MD (US); Haitao Wu, Rockville, MD (US); Gary L Griffiths, North Potomac, MD (US); Peter L Choyke, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 958 days.

(21) Appl. No.: 17/532,109

(22) Filed: Nov. 22, 2021

(65) Prior Publication Data

US 2022/0112222 A1 Apr. 14, 2022

Related U.S. Application Data

(60) Continuation of application No. 16/723,601, filed on Dec. 20, 2019, now Pat. No. 11,192,903, which is a division of application No. 15/300,883, filed as application No. PCT/US2015/023897 on Apr. 1, 2015, now Pat. No. 10,556,916.

(60) Provisional application No. 61/973,706, filed on Apr. 1, 2014.

(51) Int. Cl.

| | |
|---|---|
| ***A61K 51/04*** | (2006.01) |
| ***A61K 51/12*** | (2006.01) |
| ***C07B 59/00*** | (2006.01) |
| ***C07F 7/00*** | (2006.01) |
| ***C12Q 1/16*** | (2006.01) |
| ***G01N 33/60*** | (2006.01) |

(52) U.S. Cl.
CPC .......... *C07F 7/003* (2013.01); *A61K 51/0478* (2013.01); *A61K 51/1203* (2013.01); *C07B 59/004* (2013.01); *C12Q 1/16* (2013.01); *G01N 33/60* (2013.01); *G01N 2458/30* (2013.01)

(58) Field of Classification Search
CPC ...... A61K 51/04; A61K 51/1203; C07F 7/003
See application file for complete search history.

(56) References Cited

U.S. PATENT DOCUMENTS 4,017,596 A * 4/1977 Loberg ............... A61K 51/0478 562/571
4,612,097 A 9/1986 Jackovitz et al.
5,245,026 A 9/1993 Johnson et al.
2010/0323020 A1* 12/2010 Gokhale ................ A61K 47/02 514/235.8
2011/0142760 A1* 6/2011 Pomper .................. A61K 9/127 424/1.89

FOREIGN PATENT DOCUMENTS

| | | | | |
|---|---|---|---|---|
| EP | 0017355 B1 | * 3/1983 | | A61K 51/1203 |
| GB | 2 042887 | * 10/1980 | | |
| WO | WO 99/22026 A1 | 5/1999 | | |
| WO | WO 2004/082626 A2 | 9/2004 | | |
| WO | WO 2008/142571 A2 | 11/2008 | | |
| WO | WO 2009/056282 A1 | 5/2009 | | |
| WO | WO-2013138696 | * 9/2013 | | |
| WO | WO-2013138696 A1 | * 9/2013 | | A61K 51/0406 |

OTHER PUBLICATIONS

Bennink et al., "Evaluation of Early Treatment Response and Predicting the Need for Colectomy in Active Ulcerative Colitis With $^{99m}$Tc-HMPAO White Blood Cell Scintigraphy," *J. Nucl. Med.*, 45 (10), 1698-1704 (2004).
Botti et al., "Comparison of three different methods for radiolabelling human activated T lymphocytes," *Eur. J. Nucl. Med.*, 24 (5), 497-504 (1997).
Charoenphun et al., "[$^{89}$Zr]Oxinate$_4$ for long-term in vivo cell tracking by positron emission tomography," *Eur. J. Nucl. Med. Mol. Imaging*, 42 (2), 278-287 (2015).
Davidson-Moncada et al., "A Novel Method to Study the in Vivo Trafficking and Homing of Adoptively Transferred NK Cells In Rhesus Macaques and Humans," 56th ASH Annual Meeting and Exposition (Dec. 6-9, 2014).
Ferris et al., "Synthesis and characterisation of zirconium complexes for cell tracking with Zr-89 by positron emission tomography," *Dalton Trans.*, 43 (39), 14851-14857 (2014).

(Continued)

*Primary Examiner* — Michael G. Hartley
*Assistant Examiner* — Jagadishwar R Samala
(74) *Attorney, Agent, or Firm* — Leydig, Voit & Mayer, Ltd.

(57) ABSTRACT

The invention provides a method of preparing a $^{89}$Zr-oxine complex of the formula

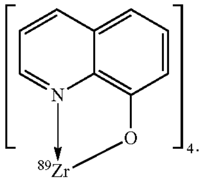

The invention also provides a method of labeling a cell with the $^{89}$Zr-oxine complex and a method for detecting a biological cell in a subject comprising administering the $^{89}$Zr-oxine complex to the subject.

9 Claims, 29 Drawing Sheets

(56) References Cited

OTHER PUBLICATIONS

Ferris, "Zirconium-89 Complexes for Cell Tracking with Positron Emission Tomography; " PhD thesis, School of Physical Sciences, University of Kent at Canterbury, pp. 1-251 (Mar. 18, 2015).
Gianotti et al., "In Vivo Evaluation of Timing, Degree, and Distribution of Bacterial Translocation Following Experimental Small Bowel Transplantation," *Transplantation*, 60 (9), 891-896 (1995).
Grupp et al., "Chimeric Antigen Receptor-Modified T Cells for Acute Lymphoid Leukemia," *N. Engl. J. Med.*, 368 (16), 1509-1518 (2013).
Holland et al., "Standardized methods for the production of high specific-activity zirconium-89," *Nucl. Med. Biol.*, 36 (7), 729-739 (2009).
International Preliminary Report on Patentability, Application No. PCT/US2015/023897, Oct. 4, 2016.
International Search Report, Application No. PCT/US2015/023897, Nov. 10, 2015.
Kater et al., "Cellular immune therapy for chronic lymphocytic leukemia," *Blood*, 110 (8), 2811-2818 (2007).
Kathirgamanathan et al., "Discovery of two new phases of zirconium tetrakis(8-hydroxyquinolinolate): synthesis, crystal structure and their electron transporting characteristics in organic light emitting diodes (OLEDs)," *J. Mater. Chem.*, 21 (6), 1762-1771 (2011).
Körbling et al., "Twenty-five years of peripheral blood stem cell transplantation," *Blood*, 117 (24), 6411-6416 (2011).
Mairal et al., "Simultaneous administration of $^{111}$In-human immunoglobulin and $^{99m}$Tc-HMPAO labelled leucocytes in inflammatory bowel disease," *Eur. J. Nucl. Med.*, 22 (7), 664-670 (1995).
Mcafee et al., "Survey of Radioactive Agents for In Vitro Labeling of Phagocytic Leukocytes. I. Soluble Agents," *J. Nucl. Med.*, 17 (6), 480-487 (1976).
Meszaros et al., "89Zr-Oxine Complex: a Long-Lived Radiolabel for Cell Tracking Using PET," 2013 World Molecular Imaging Society Conference, Presentation LBAP 024 (Sep. 10, 2013).
O'Neill et al., "Manipulating dendritic cell biology for the active immunotherapy of cancer," *Blood*, 104 (8), 2235-2246 (2004).
Palucka et al., "Cancer immunotherapy via dendritic cells," *Nat. Rev. Cancer*, 12 (4), 265-277 (2012).
Sadelain et al., "The basic principles of chimeric antigen receptor (CAR) design," *Cancer Discov.*, 3 (4), 388-398 (2013).
Sato et al., "89Zr-Oxine Complex PET Cell Imaging in Monitoring Cell-based Therapies," *Radiology*, 275 (2), 490-500 (May 2015).
Sato et al., "Cell labeling using Zr-89—comparison with In-111 oxine," 2013 World Molecular Imaging Society Conference, Presentation P 533 (Sep. 21, 2013).
Sato et al., "Generation and use of long-lasting cell labeling agent for positron emission tomography (PET) imaging," *J. Nucl. Med. Meeting Abstracts*, 55 (Supplement 1), 273 (2014).
Shi et al., "Improving the efficacy and safety of engineered T cell therapy for cancer," *Cancer Lett.*, 328 (2), 191-197 (2013).
Szajek et al., "Targetry, semi-remote processing, and quality control for routine production of Zr-89 for PET studies," *J. Nucl. Med. Meeting Abstracts*, 54 (Supplement 2), 1015 (2013).
Tarantal et al., "Radiolabeling Human Peripheral Blood Stem Cells for Positron Emission Tomography (PET) Imagine in Young Rhesus Monkeys," *PLoS One*, 8(10), e77148, p. 1-7 (2013).
Thakur et al., "Indium-111-labeled leukocytes for the localization of abscesses: preparation, analysis, tissue distribution, and comparison with gallium-67 citrate in dogs," *J. Lab. Clin. Med.*, 89 (1), 217-228 (1977).
White et al., "Patterns of Bacterial Translocation in Experimental Biliary Obstruction," *J. Surg. Res.*, 132 (1), 80-84 (2006).
Wolfs et al., "$^{18}$F-FDG labeling of Mesenchymal Stem Cells and Multipotent Adult Progenitor Cells for PET Imaging: Effects on Ultrastructure and Differentiation Capacity," J. Nucl. Med., 54 (3), 447-454 (2013).
Written Opinion of the International Searching Authority, Application No. PCT/US2015/023897, Nov. 10, 2016.

* cited by examiner

ZIRCONIUM-89 OXINE COMPLEX AS A CELL LABELING AGENT FOR POSITRON EMISSION TOMOGRAPHY

CROSS-REFERENCE TO RELATED APPLICATIONS

This patent application is a continuation of U.S. patent application Ser. No. 16/723,601, filed Dec. 20, 2019, which is a divisional of U.S. patent application Ser. No. 15/300,883, filed Sep. 30, 2016, now U.S. Pat. No. 10,556,916, which issued on Feb. 11, 2020, which is a U.S. national phase of International Patent Application No. PCT/US2015/023897, filed Apr. 1, 2015, which claims the benefit of U.S. Provisional Patent Application No. 61/973,706, filed Apr. 1, 2014, the disclosures of which are incorporated by reference.

BACKGROUND OF THE INVENTION

Cell-based therapies for cancer, involving the adoptive transfer of activated, expanded cells such as T cells, natural killer (NK) cells and dendritic cells (DCs) have proven effective in a variety of settings (K. Palucka et al., *Nature reviews. Cancer,* 2012, 12: 265-277; D. W. O'Neill et al., *Blood,* 2004, 104: 2235-2246; A. P. Kater et al., *Blood,* 2007, 110: 2811-2828; M. Korbling et al., *Blood,* 2011, 117: 6411-6416). With the emergence of genetically engineered T cells expressing chimeric antigen receptor and other T cell receptors (TCR) (S. A. Grupp et al., *N. Engl. J. Med.* 2013, 368: 1509-1518; M. Sadelain et al., *Cancer Discov.,* 2013, 3: 388-398; H. Shi et al., *Cancer Lett.,* 2012, 328: 191-197), together with interfering antibodies targeting immune-suppressive molecules, such as PD-1, there is now great interest in cell-based therapies. The efficacy of cell-based therapies, however, relies on the successful migration of cells to their respective targets, tumors, in the case of cytotoxic T cells (CTLs) or NK cells, lymphoid organs, in the case of DC vaccines, and bone marrow (BM), in the case of hematopoietic stem cells. Methods to monitor these transferred therapeutic cells, however, are currently limited, leaving uncertain the fate of these cells in patients and making it difficult to assess the impact of cell modification on trafficking to the target.

None of the current preclinical imaging techniques for tracking cells are ideal for clinical use. Bioluminescence imaging (BLI) using luciferase reporter genes and optical tagging are not practical for whole body imaging because of the limited penetration of light in tissue. Moreover, BLI requires gene transfection and carries the risk of immunogenicity related to exposure to a non-human protein. Magnetic resonance imaging with iron loaded cells has been employed but has limited sensitivity due to negative contrast superimposed on highly heterogeneous background. Radiolabeling of cells has several advantages. Because the body has no background radioactivity, very high label-to-background ratios can be achieved and whole body monitoring is possible. Cell labeling has classically employed $^{111}$In-oxine which requires single photon emission tomography (SPECT) imaging (M. L. Thakur et al., *J. Lab. Clin. Med.,* 1977, 89: 217-228; G. McAfee, M. L. et al., *J. Nucl. Med.,* 1976, 17: 480-487; L. Mairal et al., *Eur. J. Nucl. Med.,* 1995, 22: 664-670; R. J. Bennink et al., *J. Nucl. Med.,* 2004, 45: 1698-1704) with its inherently lower sensitivity and resolution compared to positron emission tomography (PET) requiring relatively high radiation doses to the labeled cells. PET is at least ten-fold more sensitive than SPECT and therefore, has the potential to reduce the exposure of labeled cells by at least one log. Fluorine-18-Fluorodeoxyglucose ($^{18}$F-FDG), a glucose analog, has been used to label cells ex vivo. Because $^{18}$F-FDG labeling relies on elevated glucose metabolism, it is not suitable for dormant or inactivated cells. Moreover, the half-life of $^{18}$F (109.7 min) significantly limits the amount of time for cell tracking. Finally, $^{18}$F-FDG is released from the cells by phosphatase activity (C. Botti et al., *Eur. J. Nucl. Med.,* 1997, 24: 497-504; E. Wolfs et al., *J. Nucl. Med.,* 2013, 54: 447-454) leading to non-specific signals. In order to track cells for at least several days, a positron emitting radioisotope with a longer half-life is required.

Thus, there remains a need in the art for methods for labeling cells with an agent that allows for tracking the cells for at least several days without significantly interfering with cell survival, proliferation, or function.

BRIEF SUMMARY OF THE INVENTION

The invention provides a method of preparing a $^{89}$Zr-oxine complex of the formula:

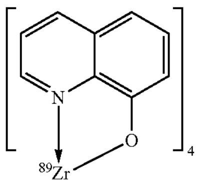

comprising (i) combining a solution of oxine and $^{89}ZrCl_4$ in hydrochloric acid at room temperature (e.g., 16-26° C., 20° C.±2° C., around 20° C.) to form a mixture, (ii) adding an alkaline solution to the mixture in an amount effective to neutralize the mixture, (iii) generating $^{89}$Zr-oxine complex, and optionally, (iv) extracting $^{89}$Zr-oxine into an organic solvent to isolate the $^{89}$Zr-oxine complex.

The invention also provides a method of labeling a cell with $^{89}$Zr-oxine comprising contacting the cell with the $^{89}$Zr-oxine complex in a buffer solution at room temperature or below.

The invention further provides a kit for labeling biological cells for PET-imaging, comprising (a) a first component comprising $^{89}$Zr, (b) a second component comprising oxine, (c) a third component comprising an alkaline solution, and (d) instructions for use.

The invention additionally provides a method of detecting a biological cell or a microorganism in a subject comprising administering to the subject a labeled biological cell or microorganism comprising the $^{89}$Zr-oxine complex and examining at least a portion of the subject by PET imaging, thereby detecting the labeled biological cell or microorganism in the subject.

The invention also provides a method of transplanting a biological cell into a subject comprising (a) administering to the subject a labeled biological cell comprising the $^{89}$Zr-oxine complex, (b) examining at least a portion of the subject by PET imaging, (c) detecting the migration pattern and/or cellular distribution pattern of the labeled biological cell in the subject, and (d) optionally administering additional biological cells.

BRIEF DESCRIPTION OF THE SEVERAL VIEWS OF THE DRAWING(S)

Figure 8A:
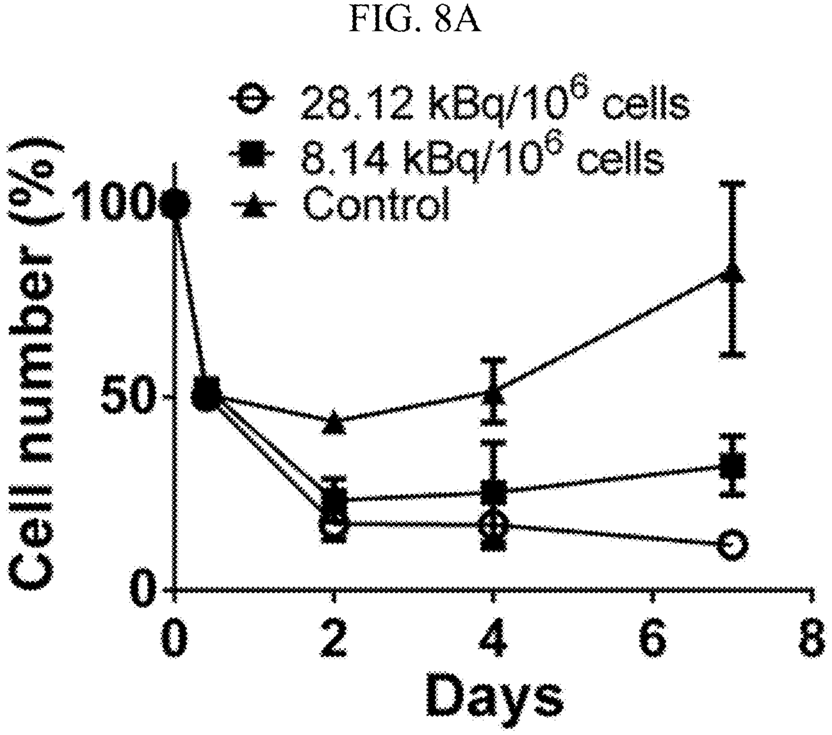

FIG. 8A demonstrates that BM cells labeled with $^{89}$Zr-oxine and cultured in stem cell factor (SCF), Fms-related tyrosine kinase 3 ligand (FLT3L), and thrombopoietin (TPO) survived and proliferated.

Figure 8B:
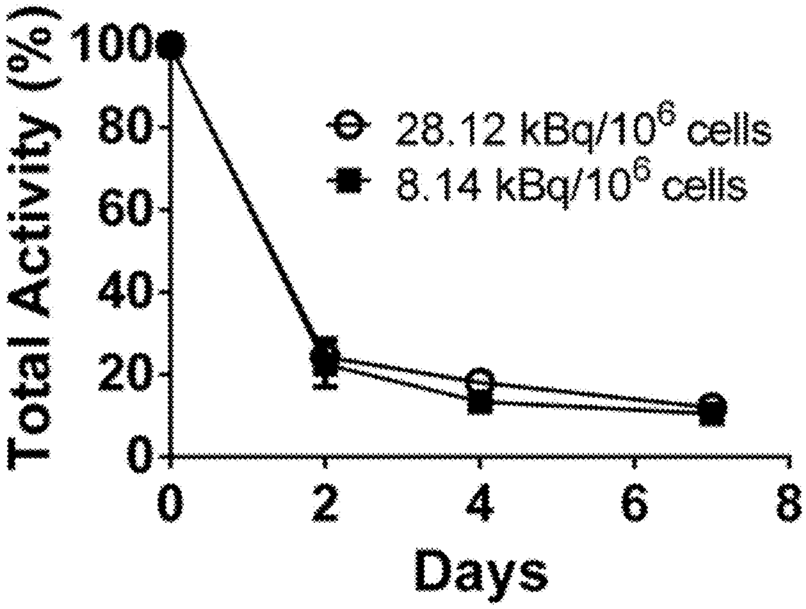

FIG. 8B depicts that total $^{89}$Zr activity associated with cells decreased as the cells died during the 0-2 day period, but remained stable as the rate of cell death decreased and cells began to proliferate after day 2.

Figure 8C:
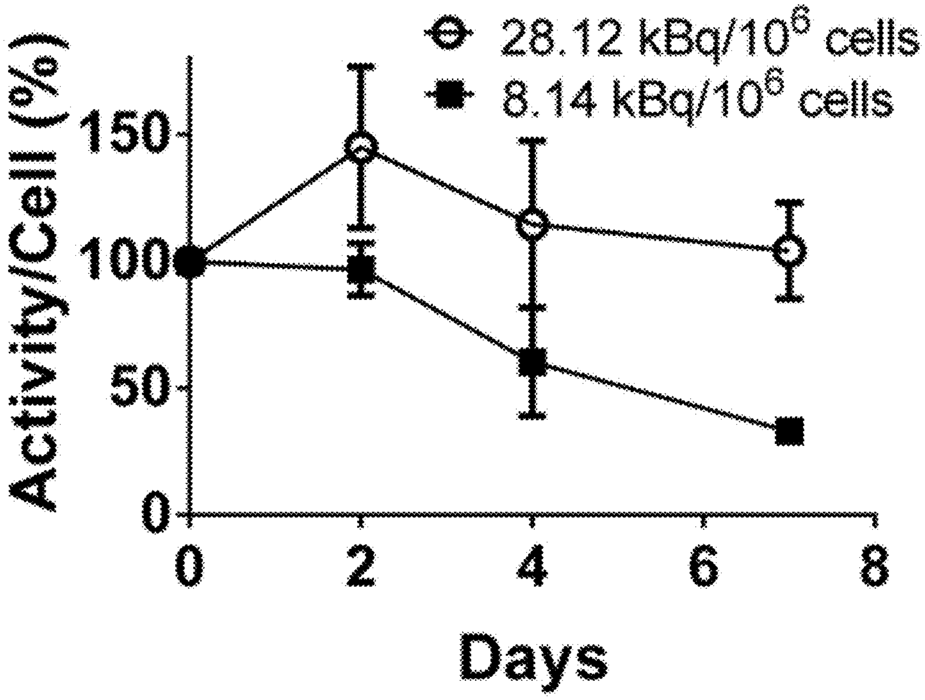

FIG. 8C demonstrates that specific activity of the $^{89}$Zr-oxine labeled BM cells decreased in the cells labeled with the lower dose as cells proliferated, but remained about the same in cells labeled with the higher dose.

Figure 9A:
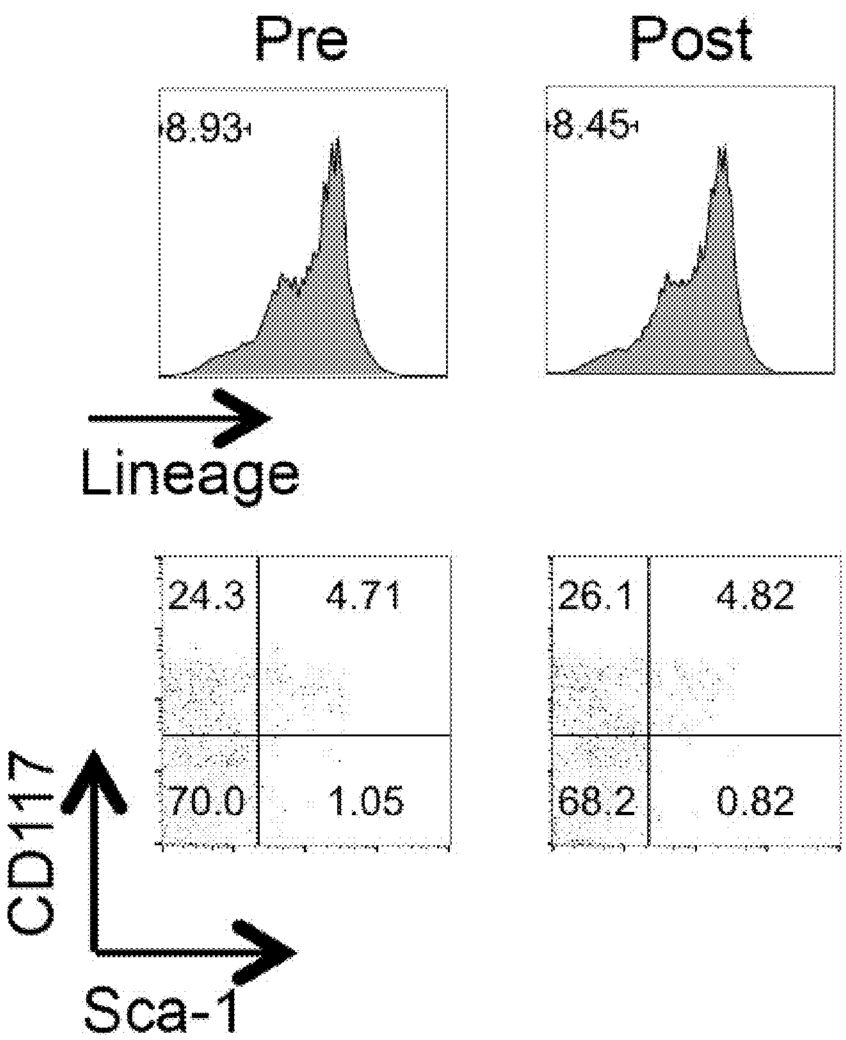

FIG. 9A demonstrates that labeling did not alter the expression of sca-1, CD117, and lineage markers in BM cells.

Figure 9B:
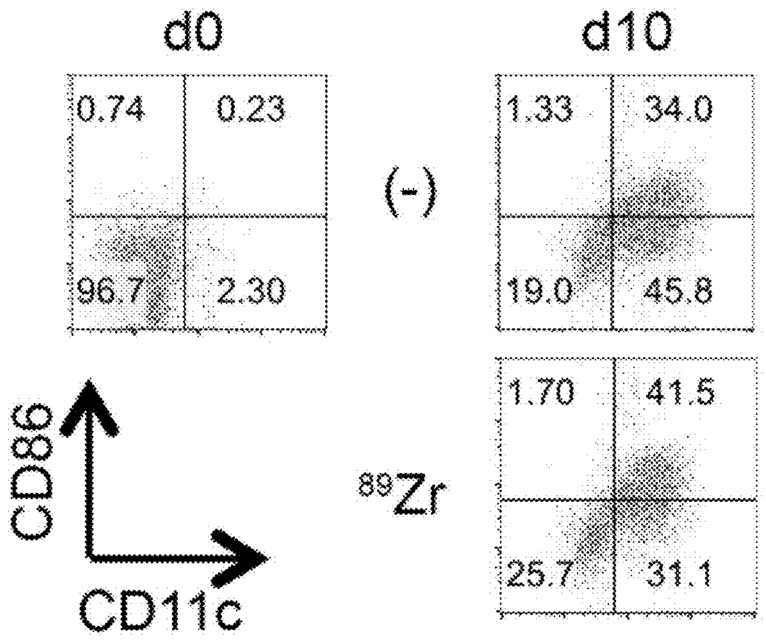
Figure 9C:
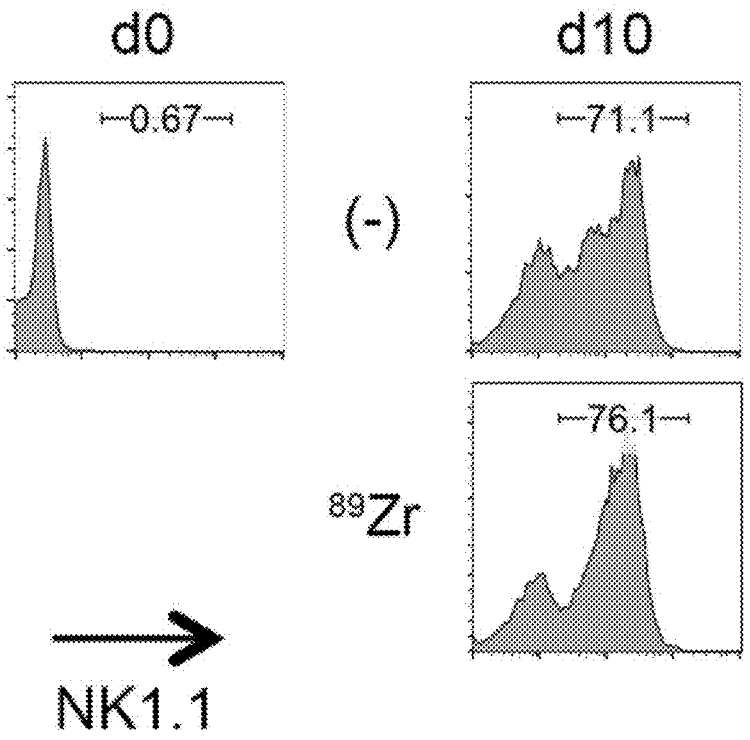

FIGS. 9B and 9C demonstrate that $^{89}$Zr-oxine labeled BM cells and non-labeled cells cultured with GM-CSF (FIG. 9B) or IL-15 (FIG. 9C) differentiated into mature DCs (FIG. 9B) and NK/NK-T cells (FIG. 9C), respectivly, in a comparable manner.

Figure 10A:
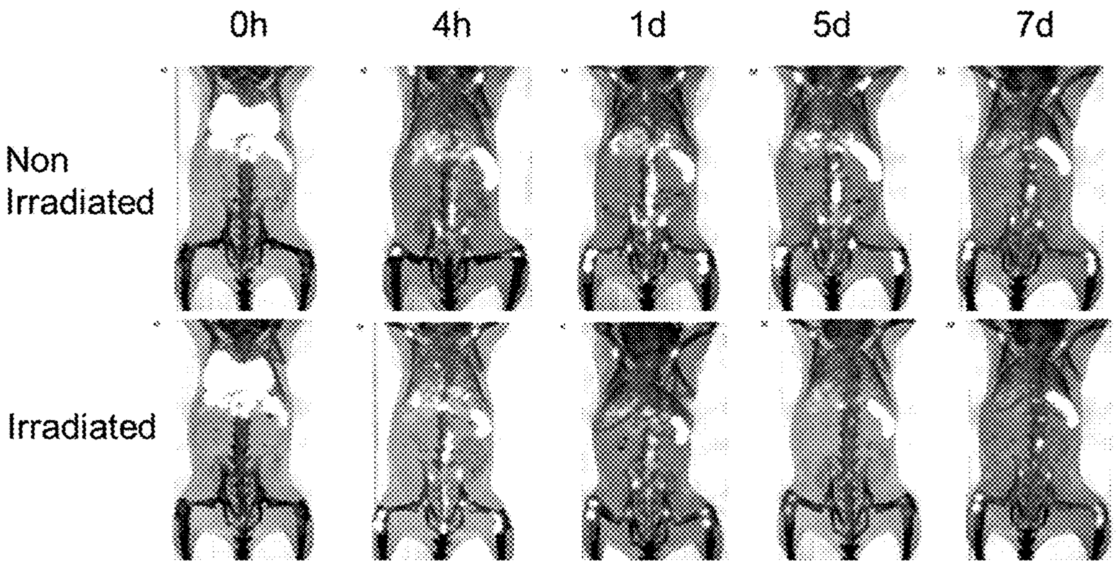

FIG. 10A is a serial microPET/CT imaging of $^{89}$Zr-oxine labeled BM cells that revealed a rapid trafficking of BM cells through the lungs to the BM, spleen, and liver.

Figure 10B:
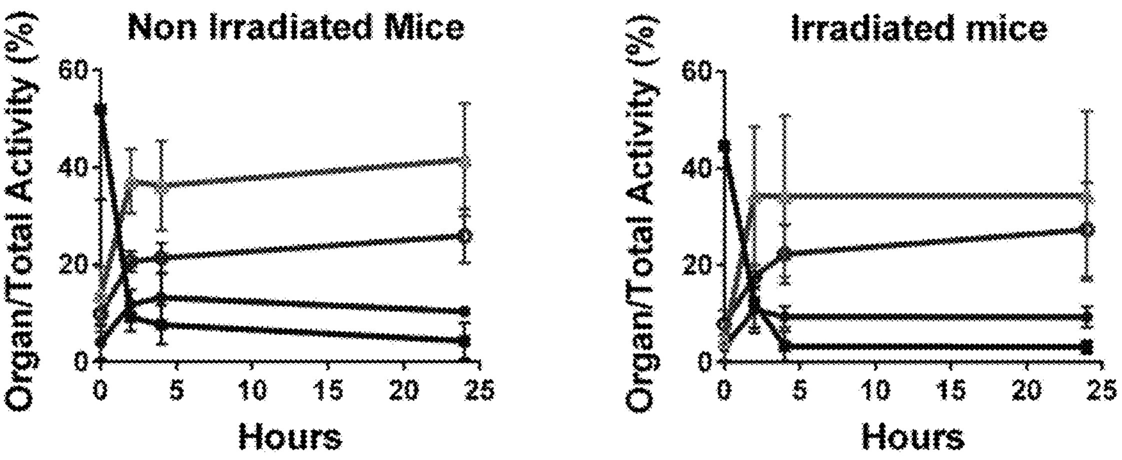

FIG. 10B illustrates the kinetics of BM cell migration to the BM in the spine (○), lungs (■), liver (▲), and spleen (•) analyzed from the PET/CT images of non-irradiated and irradiated recipient mice (n=3).

Figure 11A:
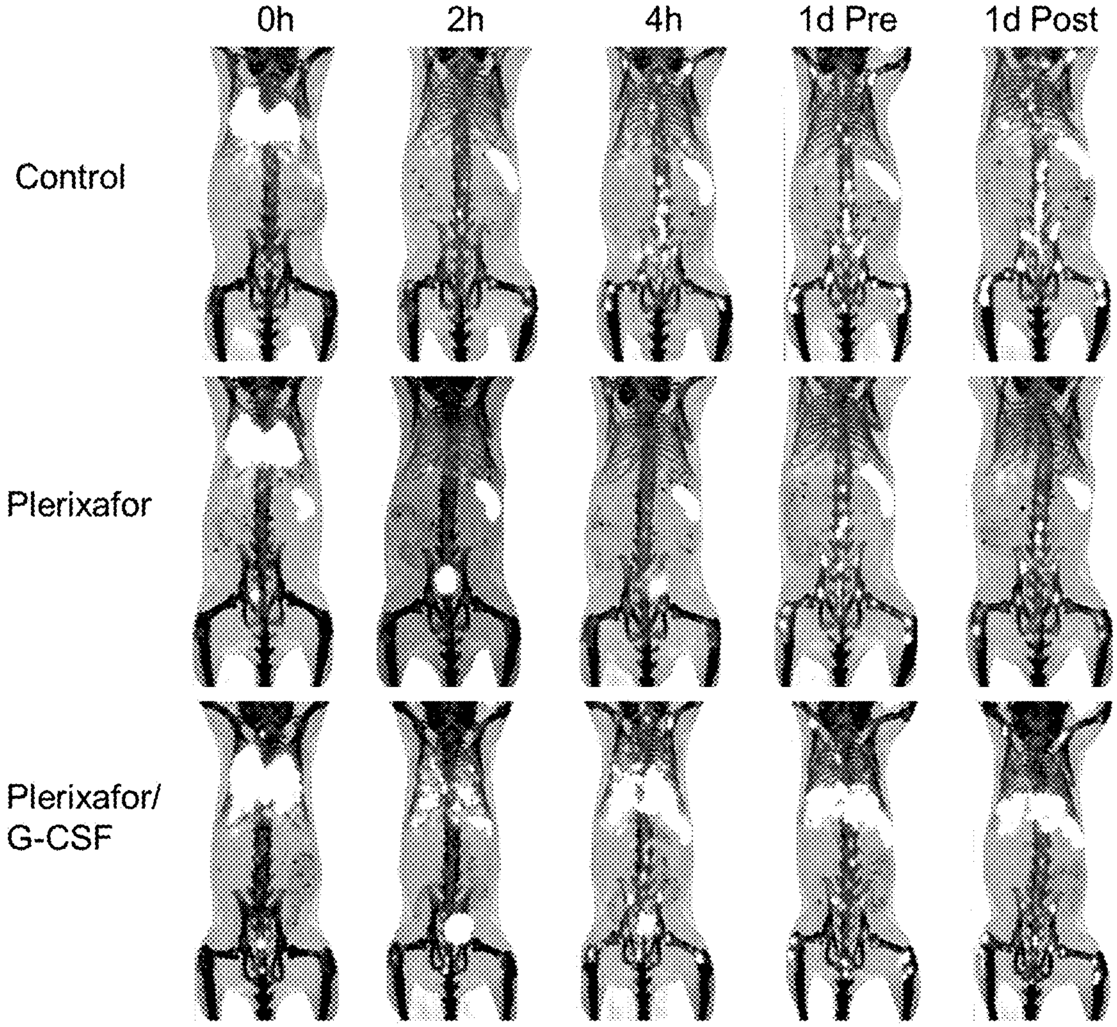

FIG. 11A illustrates that $^{89}$Zr-oxine microPET/CT imaging demonstrated CXCR4 dependent BM homing and retention within the BM of transferred BM cells. Plerixafor or plerixafor/G-CSF were injected 15 min before and 1 day after the cell transfer. "Pre" indicates 1 hour prior to plerixafor/G-CSF injection and "Post" is 1 hour after plerixafor/G-CSF injection.

Figure 11B:
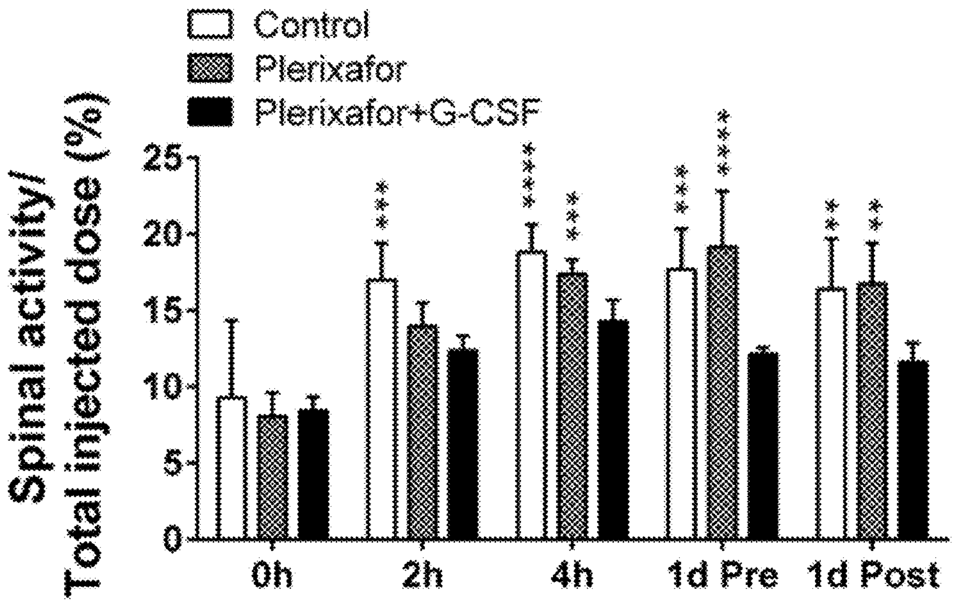

FIG. 11B is a kinetics analysis of the cell migration that demonstrated inhibition of BM homing with plerixafor at the 0-2 h time point and prolonged inhibition with plerixafor/G-CSF. All recipient mice received a lethal whole-body irradiation at 9.5 Gy 24 h prior to cell transfer. "Pre" indicates 1 hour prior to plerixafor/G-CSF injection and "Post" is 1 hour after plerixafor/G-CSF injection. Asterisks indicate a statistical significance between control 0 h group: *P<05; P<0.01; *P<0.001; <****P<0.0001.

Figure 12A:
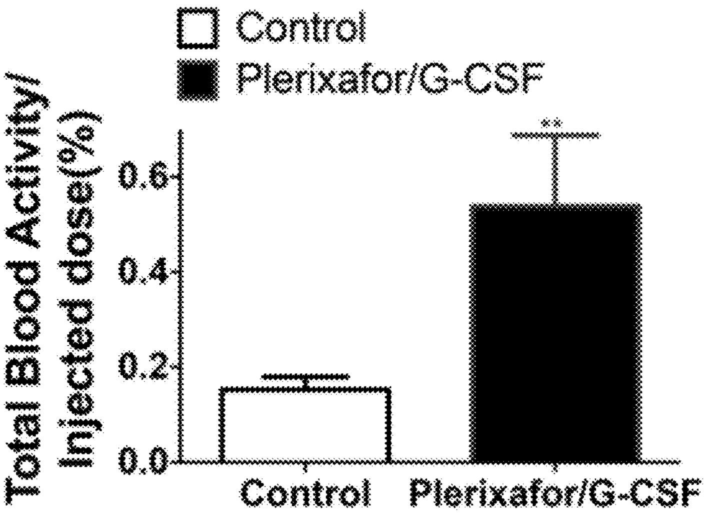

FIG. 12A demonstrates that donor GFP$^+$ BM cells labeled with $^{89}$Zr-oxine were mobilized into the blood 1 day following plerixafor/G-CSF treatment. Asterisks indicate statistical significance. **P<0.01.

Figure 12B:
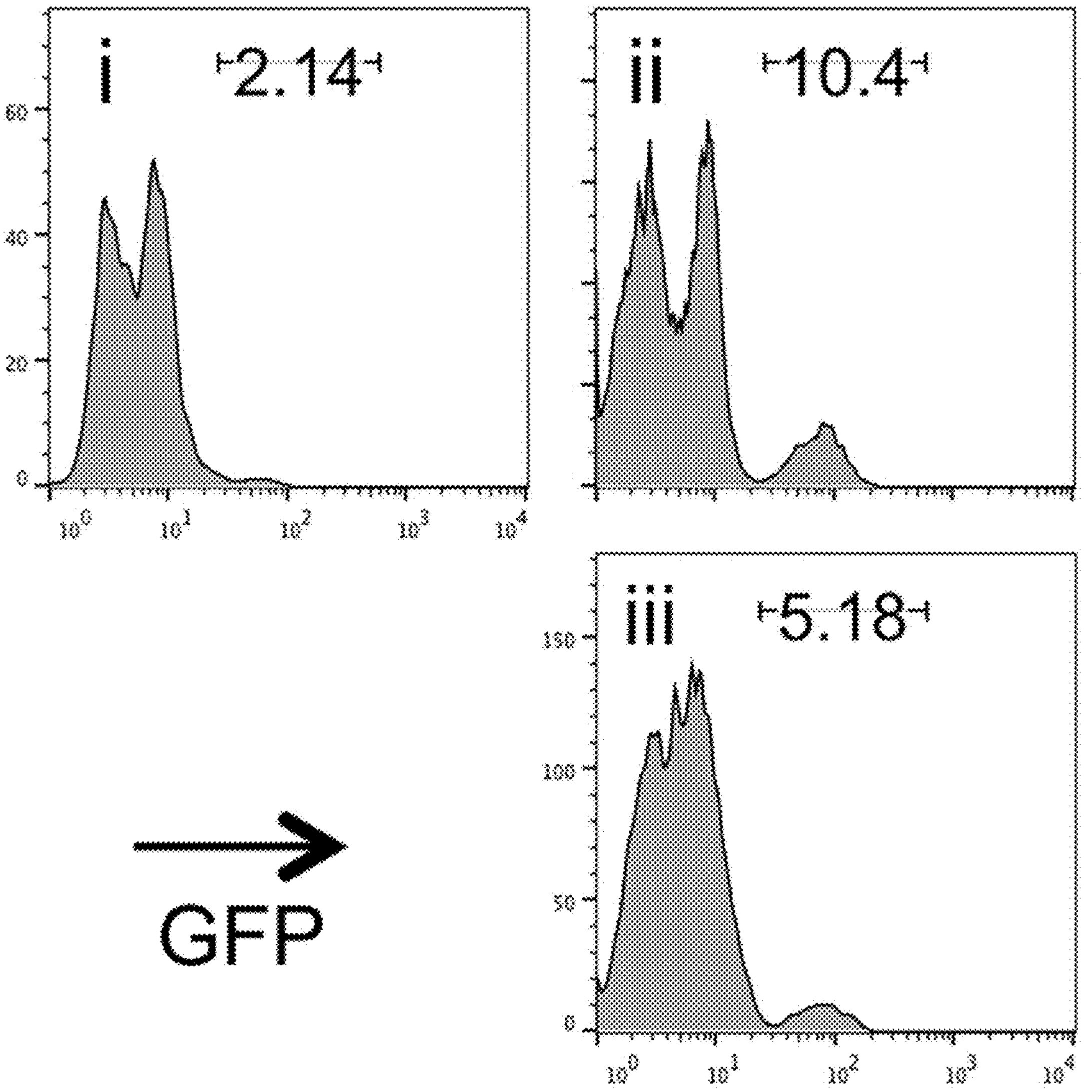

FIG. 12B is a flow cytometry analysis that confirmed mobilized donor GFP$^+$ BM cells in the circulation with some variations among the mice. Control (i) and mobilized (ii-iii) mice (n=4).

Figure 13A:
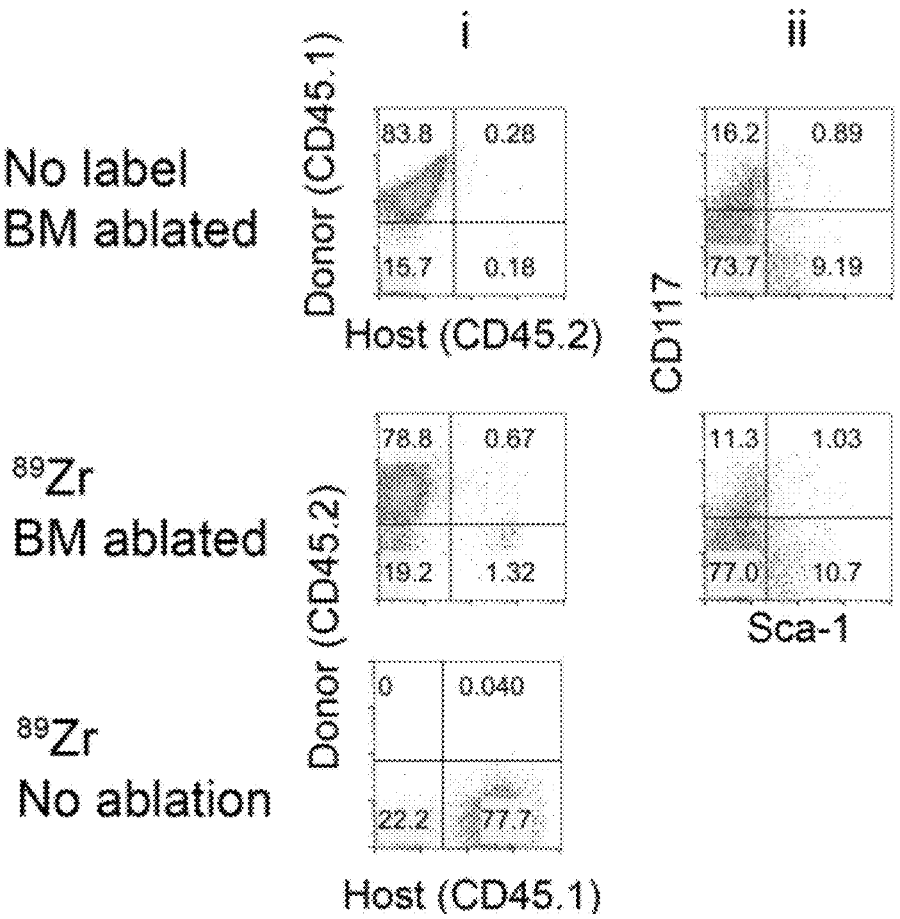

FIG. 13A demonstrates that donor derived cells reconstituted the BM of the hosts received BM ablation prior to the transplantation, but not in the non-BM ablated hosts.

Figure 13B:
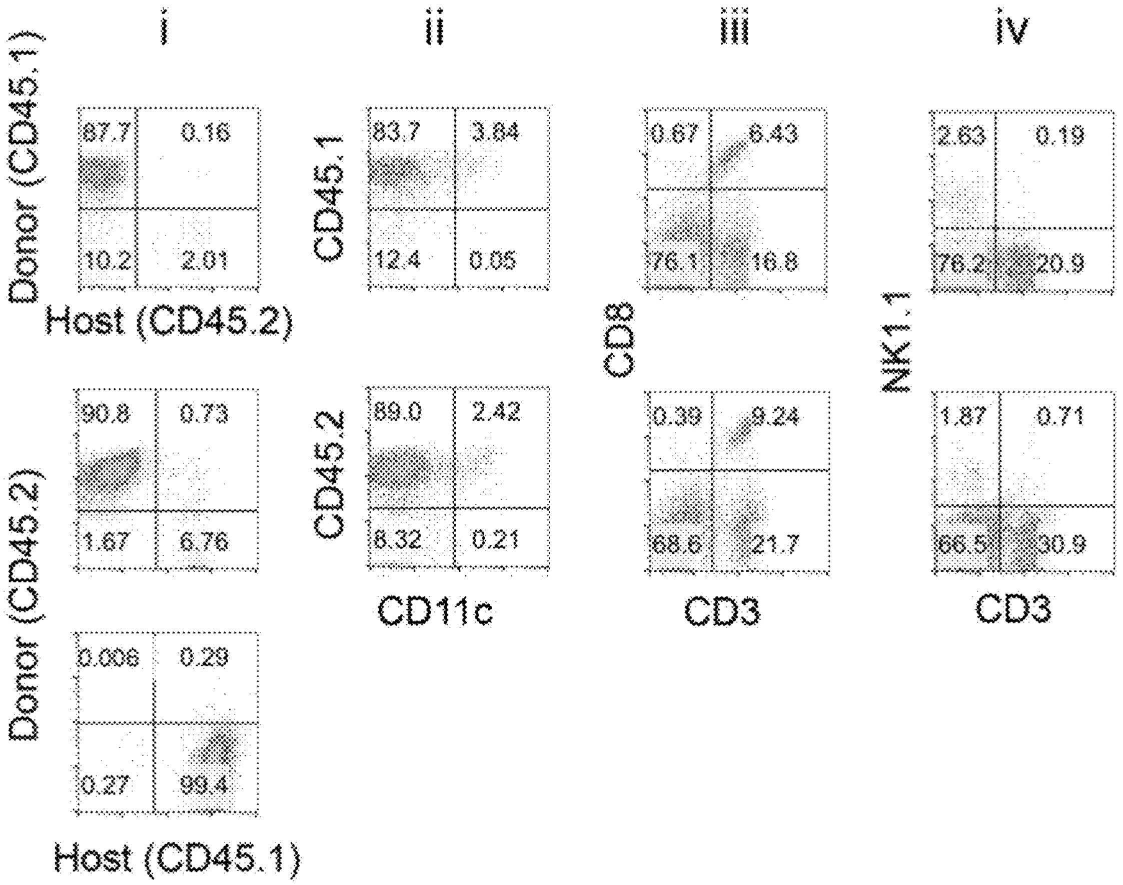

FIG. 13B is a flow cytometry analysis of splenocytes harvested from recipient mice 10 weeks following cell transfer demonstrating that BM cells had differentiated into DCs (CD11c$^+$), NK cells (CD3$^-$NK1.1$^+$), and T cells (CD3$^+$ NK1.1$^-$) in BM ablated but not in non-ablated recipient mice.

DETAILED DESCRIPTION OF THE INVENTION

The $^{89}$Zr-oxine complex described herein comprises $^{89}$Zr and oxine. Oxine is 8-hydroxyquinoline. $^{89}$Zr is produced, for example via an $^{89}$Y(pn)$^{89}$Zr or $^{89}$Y(d,2n)$^{89}$Zr reaction. In an $^{89}$Y(pn)$^{89}$Zr reaction, a proton beam with about 14 MeV energy is used to bombard a target such as a yttrium foil mounted onto an aluminum/copper disk. In a $^{89}$Y(d,2n)$^{89}$Zr reaction, about a 14 MeV deuteron beam is used to irradiate a yttrium pellet. The $^{89}$Zr is liberated from the target, typically in an acidic solution such as an oxalic acid solution. Thus, in an embodiment, the $^{89}$Zr is provided as an $^{89}$Zr-oxalic acid solution. In an embodiment, the $^{89}$Zr-oxalic acid solution can be loaded onto a chromatography column, such as a C-18 SEP-PAK™ cartridge (Waters, Milford, MA), and then eluted with aqueous hydrochloric acid to provide $^{89}Zr$ as $^{89}ZrCl_4$.

$^{89}Zr$-oxine complex can be generated in aqueous solution by conjugating oxine to $^{89}Zr$. In an embodiment, a solution of oxine in, e.g., dilute hydrochloric acid, can be combined with a solution of $^{89}ZrCl_4$ optionally in the presence of a surfactant, such as polysorbate 80 ("TWEEN™ 80") or functional equivalents thereof. The aqueous solution of $^{89}Zr$-oxine complex is suitable for use in the inventive methods disclosed herein. Optionally, the $^{89}Zr$-oxine complex can be extracted into an organic solvent such as chloroform to isolate the $^{89}Zr$-oxine complex.

In an embodiment, the $^{89}Zr$-oxine complex is used to label biological cells, particularly mammalian cells. Also included herein is a biological cell labeled with $^{89}Zr$-oxine complex. The term "biological cell" as used herein, refers to a cellular structure having biological functionality including, but not limited to, production of biological proteins, and/or induction of extracellular ligand binding sites. A biological cell can be naturally occurring or modified and is preferably viable. In a preferred embodiment, the biological cell is a healthy cell. In certain preferred embodiments, the biological cell is a T cell, a natural killer (NK) cell, a dendritic cell, a macrophage, a monocyte, a B cell, a myeloid cell, a platelet, a stem cell, a progenitor cell, a mesenchymal cell, an epithelial cell, a neural cell, a skeletal myoblast, or a pancreatic islet cell. Non-limiting examples of suitable stem cells include bone marrow-derived stem cells such as hemopoeitic stem cells, embryonic stem cells, adult stem cells, mesenchymal stem cells, epidermal stem cells, endothelial stem cells, endothelial progenitor cells, resident cardiac stem cells, induced pluripotent stem cells, adipose-derived stem cells, amniotic fluid stem cells, uterine stem cells, neural stem cells, neural progenitor cells, cancer stem cells (e.g., a leukemic hematopoietic stem cells, solid tumor stem cells), umbilical cord blood stem cells, or any combination thereof. In an embodiment, the biological cell is a bone marrow cell (e.g., a stem cell, progenitor cell). Further, a biological cell can be a cancerous cell, for example, a breast cancer cell or a leukemic cell. In an embodiment, the biological cell is genetically engineered in order to stay immortalized, to enhance the targeting property, or to enhance cellular function, or is a genetically altered vector-producing cell.

In an embodiment, the biological cell is in cell culture, that is, the cells are ex vivo. When in cell culture, the biological cell is typically in a vessel such as a culture dish that contains a nutrient broth called a culture medium. In an embodiment, biological cells are labeled by contacting the biological cells with a solution/suspension containing the $^{89}Zr$-oxine complex in an amount and for a time sufficient to label the cells with the $^{89}Zr$-oxine complex. Culture medium is defined as a liquid that covers biological cells in a culture dish and that contains nutrients to nourish and support the cells. Culture medium may include growth factors and other additives to produce desired changes in the cells.

In another embodiment, a microorganism can be tracked by labeling the microorganism with the $^{89}Zr$-oxine complex and subsequently imaged (e.g., imaged in a subject). The microorganism can be any suitable single celled or multicellular microorganism, such as an infectious pathogen or human microbiome. Examples of suitable microorganisms include viruses, viroids, bacteria (e.g., commensal bacteria), parasites, archaea, protozoa, fungus, algae, yeasts, and rotifers. In a particular embodiment, the microorganism is commensal bacteria (e.g., normal microflora, indigenous microbiota).

As used herein labeling of a cell with $^{89}Zr$-oxine complex means that the complex is inside the cell or microorganism or associated with the cell or microorganism such that the complex, and thus the cell or microorganism, can be detected such as by PET imaging.

In an embodiment, after labeling with the $^{89}Zr$-oxine complex, the cells or microorganisms are washed with a solution containing a chelator such as deferoxamine mesylate to remove any free $^{89}Zr$. Additional chelators include Deferasirox, an iron chelating medication that comes in a tablet form, hydroxyethyl starch deferoxamine (HESdeferoxamine), EDTA, and DTPA.

It was determined experimentally that cells and microorganisms can be effectively labeled with the $^{89}Zr$-oxine complex did not significantly alter cellular phenotypes, survival, proliferation, and/or function. Such improvements enable the tacking of labeled cells and microorganisms for a desired time period (e.g., several days). In an embodiment, the $^{89}Zr$-oxine complex-labeled cells or microorganisms are administered to a subject, and the labeled cells or microorganisms are then imaged by PET. For use in a therapeutic regimen, methods of administration/delivery of cells or microorganisms include injections and use of special devices to implant cells or microorganisms in various organs. The present disclosure is not limited to any particular delivery method. For example, labeled cells or microorganisms can be imaged following either a focal implantation directly into tissues, subcutaneously, subdermally, or by intravenous injection. Exemplary injection techniques include intravenous, intra-arterial, intraperitoneal and/or direct tissue injection including dermal and subdermal. Cells or microorganisms can be inserted into a delivery device that facilitates introduction by injection or implantation into the subjects. Such delivery devices include tubes, e.g., catheters, for injecting cells or microorganisms and fluids into the body of a recipient subject. In an embodiment, the tubes additionally have a needle, e.g., a syringe, through which the cells or microorganisms can be introduced into the subject at a desired location. The cells or microorganisms can be prepared for delivery in a variety of different forms. For example, the cells or microorganisms can be suspended in a solution or gel or embedded in a support matrix when contained in such a delivery device. Cells or microorganisms can be mixed with a pharmaceutically and/or diagnostically acceptable carrier or diluent in which the cells or microorganisms remain viable. Pharmaceutically and/or diagnostically acceptable carriers and diluents include saline, aqueous buffer solution, solvents, and/or dispersion media. The use of such carriers and diluents is well known in the art. The solution is preferably sterile and fluid. In specific embodiments, the solution is stable under the conditions of manufacture and storage and preserved against the contaminating action of microorganisms such as bacteria and fungi by use of preservatives. Solutions can be prepared by incorporating cells or microorganisms as described herein in a pharmaceutically and/or diagnostically acceptable carrier or diluent and, as required, other ingredients enumerated above, followed by filtered sterilization.

In certain embodiments, the $^{89}Zr$-oxine complex-labeled cells or microorganisms further comprise an MR imaging agent such as a superparamagnetic agent or fluorine-19 ($^{19}F$) agent to allow for PET-MRI. An exemplary superparamagnetic agent is a superparamagnetic nanoparticle optionally associated with a polymer. Superparamagnetism means a form of magnetism, which appears in small ferromagnetic or ferromagnetic nanoparticles. Like the paramagnetic materials, the superparamagnetic materials do not maintain their magnetism in the absence of an externally applied magnetic field. Superparamagnetic nanoparticles are particles having at least one dimension of 1 nm to 100 nm (e.g., at least 1 nm, at least 10 nm, at least 20 nm, at least 30 nm, at least 40 nm, at least 50 nm, at least 60 nm, at least 70 nm, at least 80 nm, at least 90 nm, and/or less than 100 nm, less than 90 nm, less than 80 nm, less than 70 nm, less than 60 nm, less than 50 nm, less than 40 nm, less than 30 nm, less than 20 nm, less than 10 nm, less than 5 nm, or any combination thereof) and that exhibit superparamagnetic properties. Superparamagnetic nanoparticles include iron oxide, dysprosium oxide, gadolinium oxide, manganese oxide, gold oxide, silver oxide and combinations thereof. Iron oxides include, for example $Fe_3O_4$, $\gamma$-$Fe_2O_3$, FeOOH, and $\alpha$-$Fe_2O_3$. The nanoparticle can be any shape, including sphere, rod, or platelet. An exemplary superparamagnetic agent is FERAHEME™. $^{19}$F can be used as anionic or cationic emulsions to label cells.

In an embodiment, the superparamagnetic nanoparticle is associated with a polymer. In an embodiment, the polymer substantially coats at least a portion of the nanoparticle. Without wishing to be held to any particular theory or mechanism, it is believed that the polymer can facilitate in vivo transport of the nanoparticle throughout a subject, and facilitate uptake and retention of the nanoparticles by tissues and cells. The polymer can be a natural or a synthetic polymer. Exemplary synthetic polymers include poly (acrylic acid), poly(methacrylic acid), poly(ethylmethacrylic acid), poly(butylmethacrylic acid), poly(laurylmethacrylic acid), poly(hydroxyethylmethacrylic acid), poly (hydroxypropylmethacrylic acid), poly(acrylamide), poly (isocyanate), poly(styrene), poly(ethyleneimine), poly (siloxane), poly(glutamic acid), poly(aspartic acid), poly (lysine), polypropylene glycol, poly(vinyl alcohol), poly (vinyl pyrrolidone), polyethylene oxide, derivatives thereof, and combinations thereof. Exemplary natural or semi-synthetic polymers include chitosan, dextran, carboxymethyl dextran, cellulose, hyaluronic acid, alginate, their carboxymethyl or other derivatives, and combinations thereof. The polymers can be modified to include functional groups such as carboxymethyl or hydroxymethyl groups. The polymers can also be crosslinked or grafted to other polymers. In an embodiment, the polymer is a dextran such as a carboxymethylated dextran. In a specific embodiment, the polymer associated with the superparamagnetic nanoparticle is polyglucose sorbitol carboxymethyl ether.

In a specific embodiment, the superparamagnetic nanoparticle is ferumoxytol (FERAHEME™), a superparamagnetic magnetite ($Fe_3O_4$) nanoparticle associated with a low molecular weight semi-synthetic carbohydrate, polyglucose sorbitol carboxymethyl ether, with potential anti-anemic and imaging properties. Ferumoxytol is commercially available as an aqueous colloidal drug. The overall colloidal particle size in the product commercially available from AMAG Pharmaceuticals is 17-31 nm in diameter. The chemical formula of FERAHEME™ is $Fe_{5874}O_{8752}C_{11719}H_{18682}O_{9933}Na_{414}$ with an apparent molecular weight of 750 kDa.

In another embodiment, the superparamagnetic nanoparticle is ferumoxide (FERIDEX IV™), a non-stoichiometric magnetite associated with dextran.

In an embodiment, for use as MRI contrast agents, it is preferred that the superparamagnetic complexes have a neutral or positive zeta potential in water and a negative zeta potential in balanced isotonic salt solutions. In an embodiment, the superparamagnetic complexes, such as heparin-protamine-ferumoxytol ("HPF") complexes, have a positive zeta potential of 5 to 25, more specifically 10 to 20 mV in water and/or 0 to −15 mV in isotonic salt solutions.

In certain embodiments, the $^{89}$Zr-oxine complex-labeled cells or microorganisms further comprise an MR imaging agent comprising fluorine-19 ($^{19}$F). Since biological tissues have negligible endogenous fluorine content, in vivo $^{19}$F MRI can provide an effective means of detecting labeled cells or microorganisms.

In certain embodiments, the cells or microorganisms can be contacted ex vivo with a fluorocarbon imaging reagent under conditions such that the fluorocarbon imaging reagent becomes associated with the cell or microorganism. In certain embodiments, the $^{19}$F labeling agents can be linear or cyclic perfluoropolyethers or linear or cyclic perfluorohydrocarbons. Examples of suitable $^{19}$F labeling agents include, but are not limited to, perfluorocarbon-based emulsion, perfluoropolyether emulsion, perfluoro-15-crown-5 ether (PRCE), perfluorooctyl bromide (PFOB), perfluorodecalin (PFD), trans-bis-perfluorobutyl ethylene (F-33E). These agents can label cells or microorganisms without using additional reagents to facilitate the intake.

In certain embodiments, the cells or microorganisms can be contacted with the $^{19}$F labeling agent in the presence of a reagent that enhances uptake of the $^{19}$F labeling agent. The $^{19}$F labeling agent can be provided in the form of an emulsion in water containing a surfactant. Suitable surfactants can be nonionic, anionic, or cationic surfactants, and also include phospholipids. Examples of suitable nonionic surfactants include ethylene oxide-propylene oxide block copolymers. Examples of suitable cationic surfactants include cationic lipids and protamine sulfate. An example of a suitable phospholipid is egg lecithin. Emulsions can be prepared as described in Jacoby et al., *NMR Biomed.*, 2014, 27: 261-271, and other examples of suitable $^{19}$F labeling agents and techniques are disclosed in Srinivas et al., *Trends Biotechnol.* 2010 July, 28(7): 363-370 and Temme et al., *Journal of Leukocyte Biology* Volume 95, April 2014, 689-697, the disclosures of which are incorporated totally herein by reference.

The term "detect" includes imaging to ascertain the presence or absence of a labeled molecule, cell, or microorganism, particularly by a PET technique. In an embodiment, PET, PET/CT, and/or PET-MRI allows the determination of the extent of migration of the $^{89}$Zr-oxine complex-labeled cells or microorganisms, and/or whether more cells are needed for repair or replacement of damaged tissue. The imaging information obtained will also allow clinicians to associate the clinical findings and therapeutic index as it relates to the presence of the cells or the mechanisms behind their workings in order to optimize the therapeutic regimen or the tracking of cells or microorganisms.

The $^{89}$Zr-oxine complex-labeled cells disclosed herein will allow the direct transplantation of the $^{89}$Zr-oxine complex-labeled cells, non-limiting examples of which include T cell, natural killer (NK) cell, dendritic cell, macrophage, monocyte, B cell, myeloid cell, platelet, stem cell, progenitor cell, mesenchymal cell, epithelial cell, neural cell, skeletal myoblast, or pancreatic islet cell, into tissues for purposes of immunotherapy, the treatment of malignancies and/or viral infections, investigational research purposes, monitor the healing of injuries, and/or to track the migration pattern and/or cellular distribution of the labeled cells non-invasively and repeatedly as necessary. In an embodiment, immune cells, not limited to, dendritic cells, T cells, NK cells, or other genetically altered cells are labeled with the $^{89}$Zr-oxine complex disclosed herein to non-invasively monitor their trafficking into tissues or lesions in autoimmune or inflammatory diseases, ischemic diseases of the heart and central nervous system, genetically deficient disease states, and into malignancy as part of a therapeutic approach. Local administration of the $^{89}$Zr-oxine complex can be used in conjunction with systemic immunotherapy, that is, immunotherapy or vaccine therapy provided to the whole body.

As described herein, when $^{89}$Zr-oxine complex-labeled cells or microorganisms also comprise an MR imaging agent, nuclear magnetic resonance techniques can be used to detect populations of MR imaging agent-labeled cells or microorganisms. MRI can include more sophisticated measurements, including quantitative measurements and two- or three-dimensional image generation. For example, MRI can be used to generate images of such cells. In many instances, the labeled cells are administered to a living subject. Following administration of the cells or microorganisms, some portion of the subject, or the entire subject, is examined by MRI to generate an MRI data set. A "data set" means raw data gathered during magnetic resonance probing of the subject material, as well as information processed, transformed, or extracted from the raw data. Examples of processed information include two-dimensional or three-dimensional pictorial representations of the subject material.

MRI examination can be conducted according to a suitable methodology known in the art. Many different types of MRI pulse sequences, or the set of instructions used by the MRI apparatus to orchestrate data collection, and signal processing techniques (e.g., Fourier transform and projection reconstruction) have been developed over the years for collecting and processing image data. The reagents and methods described herein are not tied to any particular imaging pulse sequence or processing method of the raw NMR signals. For example, MRI methods include spin-echo, stimulated-echo, gradient-echo, free-induction decay based imaging, and any combination thereof. The development of new and improved pulse sequence and signal processing methods is a continuously evolving field, and persons skilled in the art can devise multiple ways to image the labeled cells in their anatomical context.

In an embodiment, the $^{89}$Zr-oxine complex-labeled cells or microorganisms can also comprise an optical dye, such as a fluorescent dye containing a fluorophore, to allow for detecting the cells or microorganisms using optical techniques. Suitable optical techniques include, but are not limited to, optical imaging such as fluorescence imaging including near-infrared fluorescence (NIRF) imaging, bioluminescence imaging, or combinations thereof. A typical fluorophore is, for example, a fluorescent aromatic or heteroaromatic compound, such as a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine, a carbostyryl, a porphyrin, a salicylate, an anthranilate, an azulene, a perylene, a pyridine, a quinoline, a coumarin (including hydroxycoumarins and aminocoumarins and fluorinated derivatives thereof). Near infrared-emitting probes exhibit decreased tissue attenuation and autofluorescence (Burns et al., *Nano Letters,* 2009, 9 (1), 442-448).

Non-limiting fluorescent compounds that can be used in the present invention include, Cy5, Cy5.5 (also known as Cy5++), Cy2, fluorescein isothiocyanate (FITC), tetramethylrhodamine isothiocyanate (TRITC), phycoerythrin, Cy7, fluorescein (FAM), Cy3, Cy3.5 (also known as Cy3++), Texas Red, LightCycler-Red 640, LightCycler Red 705, tetramethylrhodamine (TMR), rhodamine, rhodamine derivative (ROX), hexachlorofluorescein (HEX), rhodamine 6G (R6G), the rhodamine derivative JA133, Alexa Fluorescent Dyes (such as Alexa Fluor 488, Alexa Fluor 546, Alexa Fluor 633, Alexa Fluor 555, and Alexa Fluor 647), 4',6-diamidino-2-phenylindole (DAPI), Propidium iodide, AMCA, Spectrum Green, Spectrum Orange, Spectrum Aqua, Lissamine, and fluorescent transition metal complexes, such as europium. Fluorescent compound that can be used also include fluorescent proteins, such as GFP (green fluorescent protein), enhanced GFP (EGFP), blue fluorescent protein and derivatives (BFP, EBFP, EBFP2, Azurite, mKalamal), cyan fluorescent protein and derivatives (CFP, ECFP, Cerulean, CyPet) and yellow fluorescent protein and derivatives (YFP, Citrine, Venus, YPet), and dyes disclosed in WO 2008/142571, WO 2009/056282, and WO 99/22026, each of which is incorporated herein in its entirety. In another embodiment, the optical dye is conjugated to a nanoparticle, for example, a silica-based nanoparticle.

Also provided are compositions comprising an $^{89}$Zr-oxine complex, including cells or microorganisms, such as an $^{89}$Zr-oxine complex-labeled cell or microorganism. The compositions can be administered in a number of ways depending upon whether local or systemic treatment is desired and upon the area to be treated. Administration can be topical, pulmonary, intratracheal, intranasal, epidermal, and transdermal, intradermal, oral, or parenteral. Parenteral administration includes intravenous, intraarterial, subcutaneous, intraperitoneal, intramuscular injection or infusion, or intracranial, e.g., intrathecal or intraventricular administration.

Compositions and formulations for parenteral, intrathecal, or intraventricular administration may include sterile aqueous solutions that may also contain buffers, diluents, and other suitable additives such as, but not limited to, penetration enhancers, carrier compounds, and other pharmaceutically and/or diagnostically acceptable carriers or excipients.

Compositions include, but are not limited to, solutions, emulsions, and liposome-containing formulations. These compositions can be generated from a variety of components that include, but are not limited to, preformed liquids, self-emulsifying solids, and self-emulsifying semisolids.

The formulations, which may conveniently be presented in unit dosage forms, can be prepared according to conventional techniques well known in the art. Such techniques include the step of bringing into association the components with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions may additionally contain other adjunct components conventionally found in pharmaceutical compositions. Thus, for example, the compositions may contain additional, compatible, pharmaceutically-active materials such as, e.g., antipruritics, astringents, local anesthetics, or anti-inflammatory agents, or may contain additional materials useful in physically formulating various dosage forms of the compositions of the present invention, such as dyes, flavoring agents, preservatives, antioxidants, opacifiers, thickening agents, and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizer, wetting agents, emulsifiers, salts for influencing osmotic pressure, buffers, colorings, flavorings and/or aromatic substances and the like which do not deleteriously interact with the active components of the formulation.

PET imaging has clear advantages for labeling cells for cell-based therapies. Compared to optical and magnetic resonance imaging using superparamagnetic agent, there is no background signal in PET. Compared to SPECT imaging, PET has a ten fold better sensitivity resulting in lower doses of ionizing radiation to these sensitive cells. An added benefit of PET is improved resolution compared to SPECT. Moreover, in the clinical setting, PET/CT can be performed in a shorter time period than SPECT/CT. The present invention provides advantageously a long lived PET emitter, with $^{89}$Zr having a half-life of 3.27 days, that is capable of safely labeling hematopoietic cells.

Herein it has been demonstrated that $^{89}$Zr-oxine complex, when incubated with at least four types of hematopoietic cells, can label the cells with sufficient efficiency to enable imaging. Since the labeling occurred at 4° C., it can be inferred that $^{89}$Zr-oxine complex does not require active cell transport and indicates that oxine conjugates can permeabilize the cell membrane. Moreover, optimal labeling occurred at room temperature (e.g., 16-26° C., 20° C.±2° C., around 20° C.), suggesting that this method of labeling should be readily translatable to the clinic. Once labeled the cells demonstrated equal viability and proliferation compared to unlabeled cells. In addition, advantageously cell expression assays performed before and after $^{89}$Zr-oxine complex labeling indicated that functionality of cells was maintained after labeling.

Imaging and biodistribution of $^{89}$Zr-oxine complex-labeled cells demonstrated preferential uptake in organs according to the cell type. For instance, after clearing the lungs, DC distributed in the liver and spleen, whereas CTLs distributed exclusively to the spleen and lymph nodes on microPET imaging. Additionally, activated OT-1 CD8 cells targeted ovalbumin expressing tumors and accumulated within the tumor on microPET ultimately resulting in a dramatic decrease in tumor size. These images could be obtained at remarkably low dose levels (e.g. 145-185 kBq or 4-5 μCi). Thus, $^{89}$Zr-oxine complex labeling resulted in the ability to track a variety of cell types using microPET scans.

The ability to label and track a wide variety of cells is of potential importance to improving cell based therapies. For instance, in the case of bone marrow transplants, modifying conditions to result in increased uptake of transplanted cells in the bone marrow is considered desirable. $^{89}$Zr-oxine complex could be used to determine whether modifications to cells, methods of delivery (e.g. intravenous vs. intrabone marrow), and adjuvant therapies, increases the number of engrafted cells. For tumor targeting therapies, the effect of cell modification on tumor targeting has clear implications for the success of these therapies. Thus, the inventive method could be a useful tool across a broad range of cell-based therapies.

In an embodiment, the invention provides a kit for the labeling of biological cells or microorganisms. The kit comprises (a) a first component comprising $^{89}$Zr, (b) a second component comprising oxine, (c) an alkaline solution, and (d) instructions for use. In an embodiment, the kit further comprises at least one other labeling agent (e.g., a superparamagnetic nanoparticle, $^{19}$F and/or an optical dye). In an embodiment, the $^{89}$Zr is in a first container and the oxine is in a second container. In an embodiment, the alkaline solution is in a third container. In any of these embodiments, the kit can further comprise at least one surfactant, such surfactants known in the art and those described herein.

For purposes of the present invention, the term "subject" preferably is directed to a mammal. Mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human.

The following examples further illustrate the invention but, of course, should not be construed as in any way limiting its scope.

Materials and Methods

Mice and Cells

C57BL/6 (WT), Rag1 deficient (Rag1KO) and OT-1 T cell receptor transgenic mice against ovalbumin (OVA) were purchased from Jackson Laboratories (Bar Harbor, ME). Male and female C57BL/6 wild type (expressing CD45.2) and congenic (expressing CD45.1) mice and green fluorescence protein (GFP) transgenic mice were purchased from Jackson Laboratories (Bar Harbor, ME). All animal experiments were performed in compliance with the NIH Guide for the Care and Use of Laboratory Animals.

Cells were grown in RPMI 1640 medium (Life Technologies, Grand Island, NY) supplemented with 10% fetal calf serum (FCS), 1% penicillin-streptomycin and 50 μM 2-mercaptoethanol (Sigma-Aldrich, St. Louis, MO). DCs were differentiated from the bone-marrow of WT mice using granulocyte colony stimulating factor (20 ng/ml, GM-CSF, Peprotech, Rocky Hill, NJ). Activation of DCs was induced by lipopolysaccharide (LPS, 5 ng/ml, Sigma-Aldrich) overnight on day 5 or 6, with or without OVA peptide (SIINFEKL, 1 μg/ml, AnaSpec, Fremont, CA), and used on the following day. Naïve CD8 T cells were purified from the spleen of WT mice using magnetic beads following the manufacturer's instructions (Miltenyi, Auburn, CA). Splenocytes from OT-1 mice were activated with OVA peptide for 3 days, washed with phosphate buffered saline (PBS), and further cultured with mouse IL-2 (1 nM, Peprotech) for 2 days. Expanded cells were more than 99% CD8 T cells. NK cells were differentiated from the bone marrow of a WT mouse using 25 nM human IL-15 (Peprotech). The culture consisted of >95% NK cells ($NK1.1^+$, $CD3^-$) after depletion of NKT cells using anti-CD3 magnetic beads (Miltenyi). EL4 murine lymphoma cell lines were obtained from American Type Culture Collection (Manassas, VA). B16 murine melanoma cells expressing OVA were a gift from Drs. John Frelinger and Edith Lord.

Murine granulocyte-colony stimulation factor (G-CSF) and granulocyte macrophage-colony stimulation factor (GM-CSF), and human interleukin 15 (IL-15) were purchased from Peprotech (Rocky Hill, NJ). Murine stem cell factor (SCF), Fms-related tyrosine kinase 3 ligand (FLT3L) and thrombopoietin (TPO) were purchased from R&D Systems (Minneapolis, MN). BM cells were flushed from femurs and tibias of mice. The cells were cultured in RPMI 1640 media (Life Technologies, Grand Island, NY), supplemented with 2 mM L-glutamine, 100 IU/mL penicillin, 100 μg/mL streptomycin (Life Technologies), 10% fetal calf serum (Gemini Bio Products, Sacramento, CA) and 50 μM 2-mercaptoethanol (Sigma Chemical, St. Louis, MO), at 37° C. in 5% $CO_2$.

Antibodies and Reagents

Antibodies were purchased from eBiosciences (San Diego, CA). LPS was purchased from Sigma Aldrich. Naïve OT-1 CD8 T cells were labeled with 5-chloromethylfluorescein diacetate (CMFDA, Life Technologies) following the manufacturer's instruction before transfer to WT mice.

Activation of $^{89}$Zr-Oxine Complex Labeled Cells

After $^{89}$Zr-oxine complex labeling, DCs were stimulated with LPS (5 ng/ml) overnight. CD8 T cells labeled with $^{89}$Zr-oxine complex were stimulated with plate coated anti-CD3 antibody (10 μg/ml) and anti-CD28 antibody (5 μg/ml) for 3 days, then transferred to an antibody-free culture supplemented with human IL-15 (3 nM).

Determination of Viability of Cells and Release of $^{89}$Zr from Dead Cells

One million DCs or CTLs were labeled with $^{89}$Zr-oxine complex and washed. Cells were cultured in medium supplemented with GM-CSF (20 μg/ml) for DCs or TCR-activated for CTLs. At various time points, the number of surviving cells was counted by a Countess Automated Cell Counter (Invitrogen Corp., Carlsbad, CA) using the trypan blue exclusion method. Using another set of labeled cells, radioactivities of the cell pellet were measured by a γ-counter to determine the activity released from the cells vs. activity retained in the cells. Three activity standards were also counted each time for the decay correction.

Determination of the Functionality of $^{89}$Zr-Oxine Complex Labeled Cells

CTLs, both labeled and unlabeled, were activated by plate coated anti-CD3 antibody (10 μg/ml) and anti-CD28 antibody (5 μg/ml) for 1.5 day and expression of CD3, CD8, CD44, CD25, CD69, INF-γ and IL-2 which was evaluated by flow cytometry. Bone marrow-derived DCs on day 6 of culture with or without $^{89}$Zr-oxine complex labeling were stimulated with LPS (1 ng/ml) overnight and surface expression of CD11c, CD80, CD86, CD40, MHC class I and MHC class II was examined. In another experiment, $^{89}$Zr-labeled DCs were stimulated with LPS in the presence of OVA overnight, transferred to Rag1KO mice expressing Ly5.2 (2 million cells) pre-injected with CMFDA labeled OT-1 CD8 T cells expressing Ly5.1. Peripheral blood and splenocytes were collected 3.5 days later and dilution of CMFDA in OT-1 T cells was analyzed using flow cytometry gated on Ly5.1+CD8 T cells.

Tracking of the $^{89}$Zr-Labeled DCs and T Cells by microPET

Five million $^{89}$Zr-labeled DCs and CTLs (148-185 kBq or 4-5 μCi in 200 μl PBS) were transferred to mice via a tail vein injection. Imaging was performed using a microPET/CT imager (BioPET, Bioscan, Washington, DC) up to 7 days after the injection. Using a 400-700 keV energy window, a 5-90 min-emission scan per bed position; a total of two bed positions were scanned at 0 h-day 7. Images were reconstructed by a 3-dimensional ordered-subsets expectation maximization (3D-OSEM) algorithm. The maximum intensity projection images were fused with CT images using InVivoScope software (Bioscan, Washington, DC).

Statistical Analysis

All experiments were performed in triplicates or repeated more than three times.

The P-values were calculated by Friedman test for analysis of $^{89}$Zr-oxine labeled BM cell survival. Wilcoxon matched-pairs signed rank test was used to analyze $^{89}$Zr total activity retention and specific activity in the cells. Two-way analysis of variance followed by Tukey's multiple comparisons test correction was used for examining the effect of plerixafor and G-CSF on BM homing, and an unpaired two-tailed t-test for analyzing the effects of plerixafor/G-CSF BM mobilization into the blood.

The P-values were calculated by two-way ANOVA using GraphPad Prism software (GraphPad Software, Inc., La Jolla, CA) and P-values less than 0.05 were considered significant.

EXAMPLE 1

This example demonstrates a synthesis of $^{89}$Zr-oxine complex, in accordance with an embodiment of the invention.

$^{89}$Zr was produced at the institutional Cyclotron Facility utilizing the nuclear reaction Y(p, 2n)$^{89}$Zr and an in-house GE PETtrace beam-line (GE Healthcare) (L. Szajek et al., *J. Nucl. Med. Meeting Abstracts,* 2013, 54: 1015). Briefly, adapting a previously described method (J. P. Holland et al., *Nucl. Med. Biol.,* 2009, 36: 729-739), yttrium metal mesh (200 mg) target cups were bombarded with 13 MeV protons on a GE PETtrace. The irradiated target metal was dissolved with 6N hydrochloric acid (HCl, 2 ml), and 10 M hydrogen peroxide (0.1 ml) at 100° C. for 1 h. After dilution with water the $^{89}$Zr solution was absorbed onto a hydroxamate resin column. After washing the column with 2N HCl followed by water, $^{89}$Zr was eluted as oxalate with 1M oxalic acid in greater than 96% radiochemical yield (<0.2% $^{88}$Zr at end of bombardment). $^{89}$Zr-oxalate solution was loaded onto a pre-treated C-18 Sep-Pak cartridge and washed with $H_2O$. $^{89}ZrCl_4$ was obtained after elution with 1N HCl (0.5 ml).

Non-radioactive zirconium-oxine standard was synthesized according to a method reported previously using Zr $(i\text{-}PrO)_4$ in THF (P. Kathirgamanathan et al., *J Mater Chem,* 2011, 21: 1762-1771). HPLC was performed using a Beckman Gold HPLC system equipped with a Model 126 programmable solvent module, a Model 168 variable wavelength detector, a β-Ram Model 4 radioisotope detector, and Beckman System Gold remote interface module SS420X, using 32 KARAT™ software (Beckman Coulter, Brea CA). Analyses were performed on a Waters STYRAGEL™ HT 1 (7.8×250 mm, 5 μm) column. Tetrahydrofuran (THF) solvent was used at 0.8 mL/min flow rate. $t_R$ (Oxine)=9.34 min; $t_R$ (Zr-oxine)=8.0 min.

$^{89}$Zr-oxine complex was generated by conjugating oxine to $^{89}$Zr. Oxine in 0.04N HCl (102 μl, 20 mM) and $^{89}ZrCl_4$ (60 μl, 25.9-40.5 MBq or 700-1500 μCi) were mixed in the presence of 4 μl of 20% TWEEN™ 80. To this solution, 500 mM $NaHCO_3$ (220 μl) was added while vortexing to adjust the pH to 7-7.2 and thereby allow chelation of $^{89}$Zr by oxine to take place while neutral oxine was released from its acidic forms. To determine the conjugation yield, a small fraction of reaction mixture was extracted with chloroform. The synthesis of $^{89}$Zr-oxine complex was accomplished with >97% yield, by HPLC analysis and by determining radioactivity levels in the chloroform and aqueous phases using a dose calibrator/gamma counter.

EXAMPLE 2

This example demonstrates $^{89}$Zr-oxine complex cell labeling in accordance with an embodiment of the invention.

The cell labeling efficiency of $^{89}$Zr-oxine complex was examined in vitro as follows. A solution of $^{89}$Zr-oxine complex (88-740 kBq or 2.4-20 μCO and cell suspension (1 million cells) in PBS were incubated at room temperature (RT) for 15 min at 1:25 or 1:50 volume ratios. In some experiments, the labeling was performed in serum free medium or in complete medium at 37° C. or at 4° C. After the incubation, the cells were washed with complete medium twice and transferred to a fresh tube and washed again with PBS. Optionally, the labeled cells were washed, separately or together, with solutions containing dilute concentrations of scavenging chelating agents such as EDTA, DTPA, or desferoxamine in order to remove any membrane-bound or loosely bound $^{89}$Zr resulting from incompletely internalized $^{89}$Zr-oxine complex.

For in vivo imaging, 5 million cells were labeled using 2.96 MBq of $^{89}$Zr-oxine complex per mouse at 1:25 volume ratios.

EXAMPLE 3

This example demonstrates that $^{89}$Zr-oxine complex labeling does not depend on active cellular incorporation.

Figure 1A:
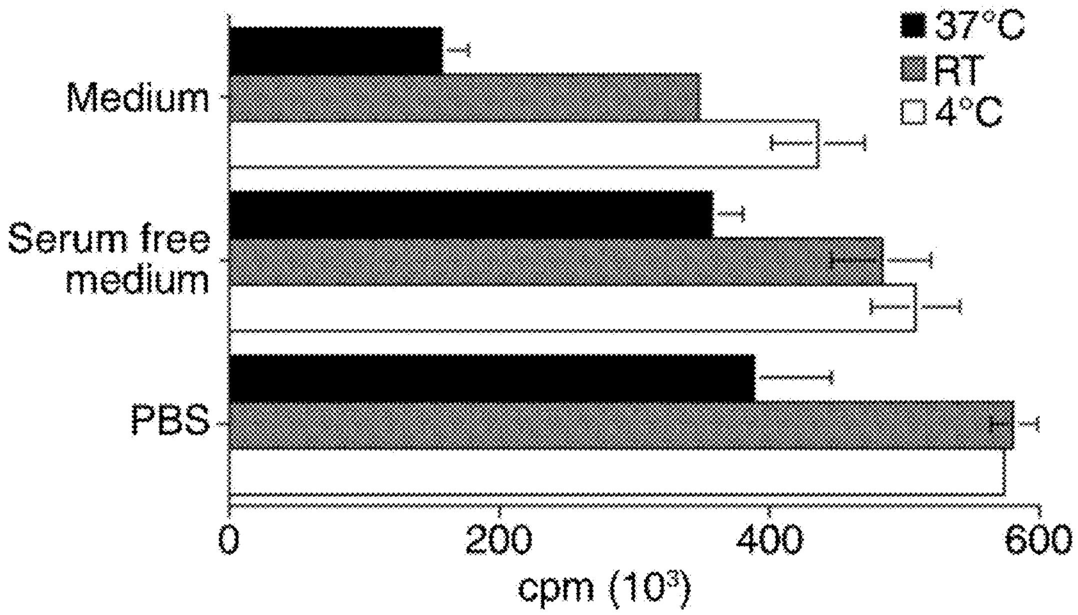
FIG. 1A illustrates the cell labeling efficiency of $^{89}$Zr-oxine complex in EL4 cells in PBS, serum free medium or in complete medium.

To determine the optimal temperature for labeling cells with $^{89}$Zr-oxine complex, cell labeling was compared at 37° C., room temperature (RT) and 4° C. using EL4 cells. One million EL4 cells were incubated with $^{89}$Zr-oxine complex at 1:50 volume ratios in PBS, serum free medium, or in complete medium at 37° C., room temperature, or 4° C. for 15 min. Radioactivities associated with the cells were determined, and the results illustrated in FIG. 1A. The highest labeling efficiency was achieved when cells were incubated with $^{89}$Zr-oxine complex at RT or at 4° C. in PBS. This suggests that cell labeling does not depend on cellular active transport. The use of serum free medium did not significantly decrease the labeling compared to PBS when labeling was performed at RT or at 4° C. Using complete cell media at RT or at 4° C., the labeling efficiency decreased to about two thirds of that achieved in PBS. The labeling at 37° C. was low under all media conditions.

EXAMPLE 4

This example demonstrates that $^{89}$Zr-oxine complex-labeled DCs and CTLs as examples of cells commonly used in cell-based therapies.

Figure 1B:
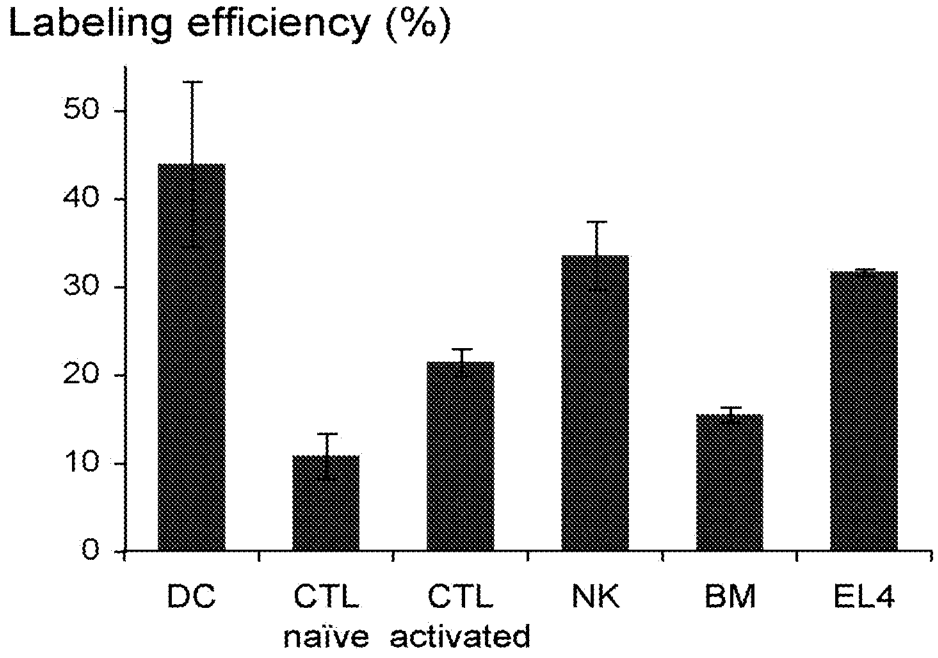
FIG. 1B illustrates the cell labeling efficiency of $^{89}$Zr-oxine complex in dendritic cells (DCs), naïve cytotoxic T cells (CTLs), activated CTLs, natural killer (NK) cells, bone marrow (BM) cells, and EL4 murine lymphoma cells.
Figure 1C:
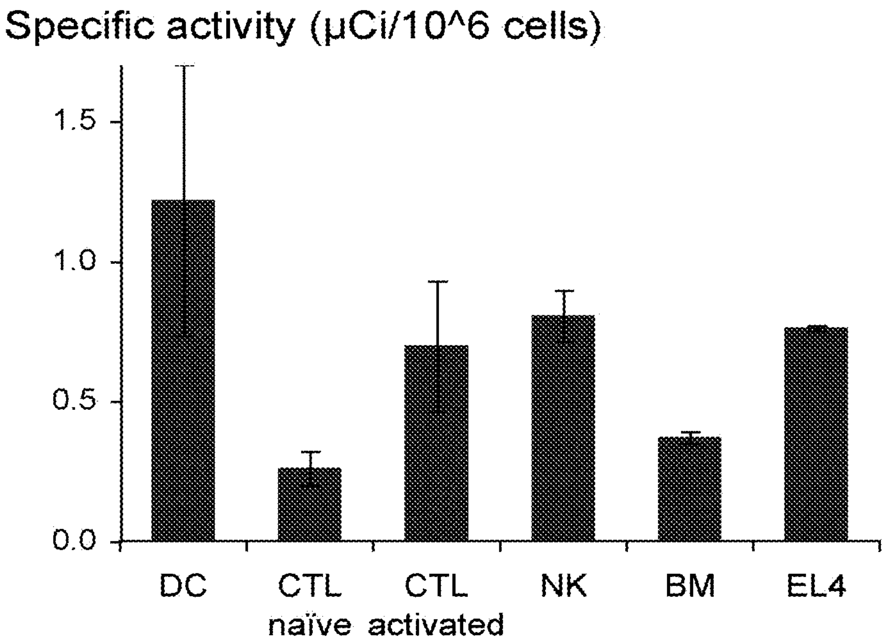
FIG. 1C illustrates the specific activity of DCs, naïve CTLs, activated CTLs, NK cells, BM cells, and EL4 murine lymphoma cells labeled with $^{89}$Zr-oxine complex.

Both cell types could be labeled with $^{89}$Zr-oxine complex although the labeling efficiency was higher with DCs (44%) than CTLs, as illustrated in FIG. 1B. When naïve and activated CTLs were compared, naïve T cells showed lower labeling efficiency (11%) than activated CTLs (21%), which was also reflected in the specific activity of the cells, as illustrated in FIG. 1C. NK cells grown with IL-15 and EL4 mouse lymphoma cells showed higher labeling efficiency and specific activity than primary CTL cells.

EXAMPLE 5

This example demonstrates that labeling with $^{89}$Zr-oxine complex did not interfere with cell survival or proliferation.

Figure 2A:
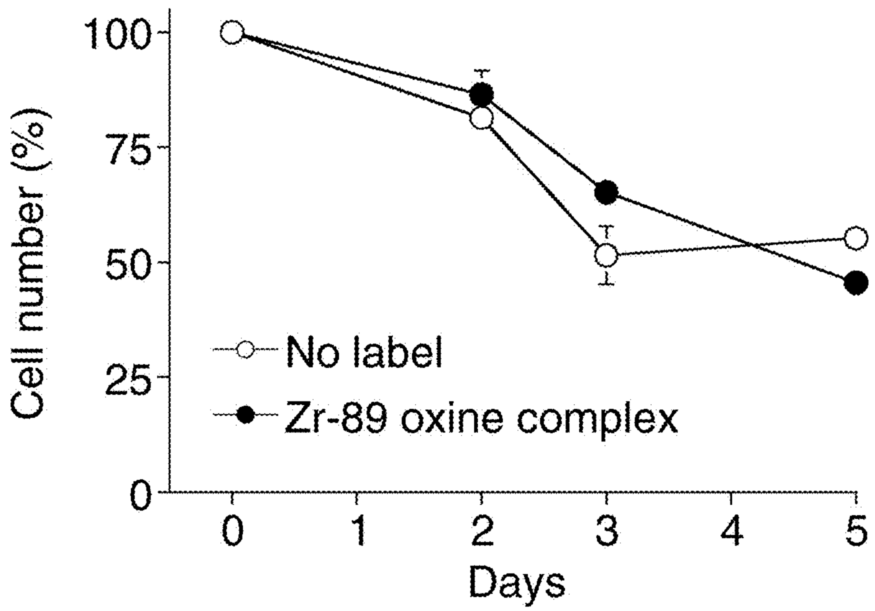
FIG. 2A illustrates viability of DCs with and without $^{89}$Zr-oxine complex labeling up to 5 days after the labeling in culture with granulocyte macrophage colony stimulation factor (GM-CSF).
Figure 2B:
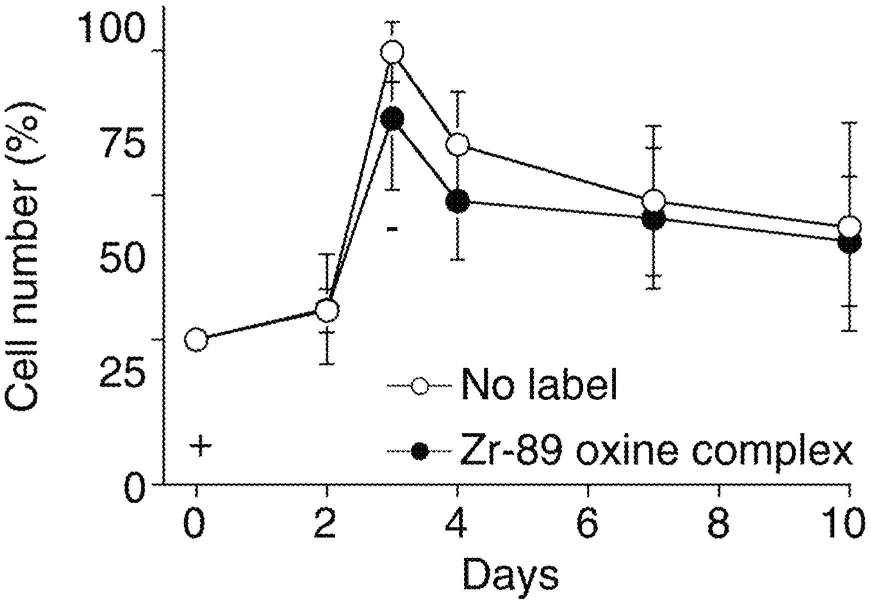
FIG. 2B shows that CTLs with and without $^{89}$Zr-oxine complex labeling underwent similar proliferation upon TCR stimulation followed by a contraction phase after withdrawal of the TCR stimulation.

Because it is critical that the labeled cells remain viable and functional, the survival of the cells after the labeling was examined. DCs labeled with $^{89}$Zr-oxine complex demonstrated similar survival as compared to non-labeled control cells when cultured with GM-CSF up to 5 days after the labeling (FIG. 2A). In addition, proliferation was also examined for CTLs labeled with $^{89}$Zr-oxine complex. Labeled CTLs rapidly proliferated upon TCR stimulation and underwent contraction when the stimulation was terminated, similarly to the non-labeled controls (FIG. 2B).

Figure 2C:
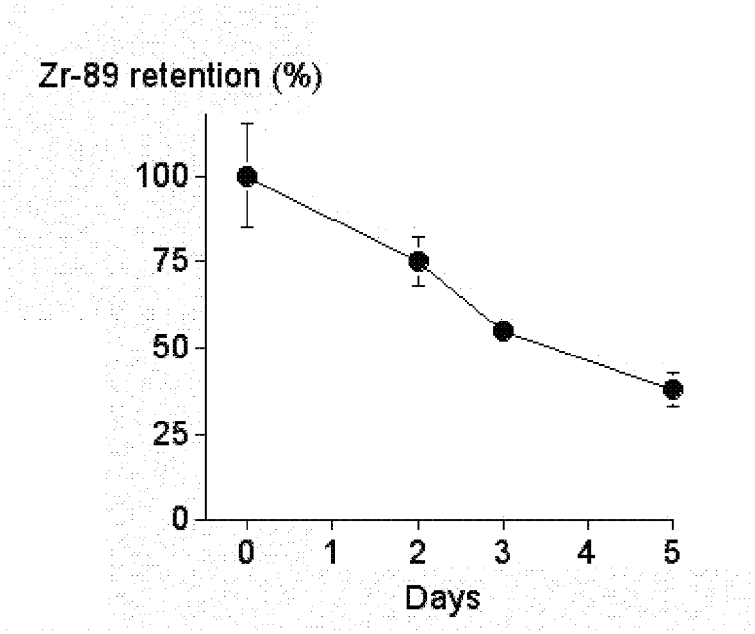
FIG. 2C shows that $^{89}$Zr-oxine complex associated with DCs paralleled the number of surviving DCs.
Figure 2D:
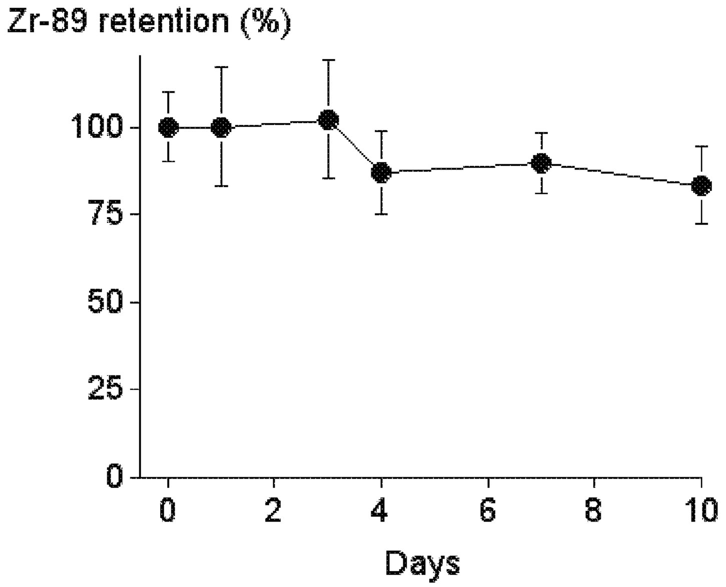
FIG. 2D shows that $^{89}$Zr-oxine complex was retained in the CTLs during the rapid proliferation, but decreased during the contraction phase in which cell number decreased.

Activity associated with $^{89}$Zr-oxine complex bound to DCs was stable and mirrored the number of DCs (FIGS. 2A and 2C). Total radioactivity associated with the CD8 T cells did not decrease while T cells underwent cell division (FIG. 2D), but decreased during the contraction phase. These results suggest that the $^{89}$Zr, once incorporated, remains in the cells during the cell division, but is likely released upon cell death.

EXAMPLE 6

This example demonstrates that labeling with $^{89}$Zr-oxine complex did not interfere with functionality of DCs and CTLs.

Figure 3A:
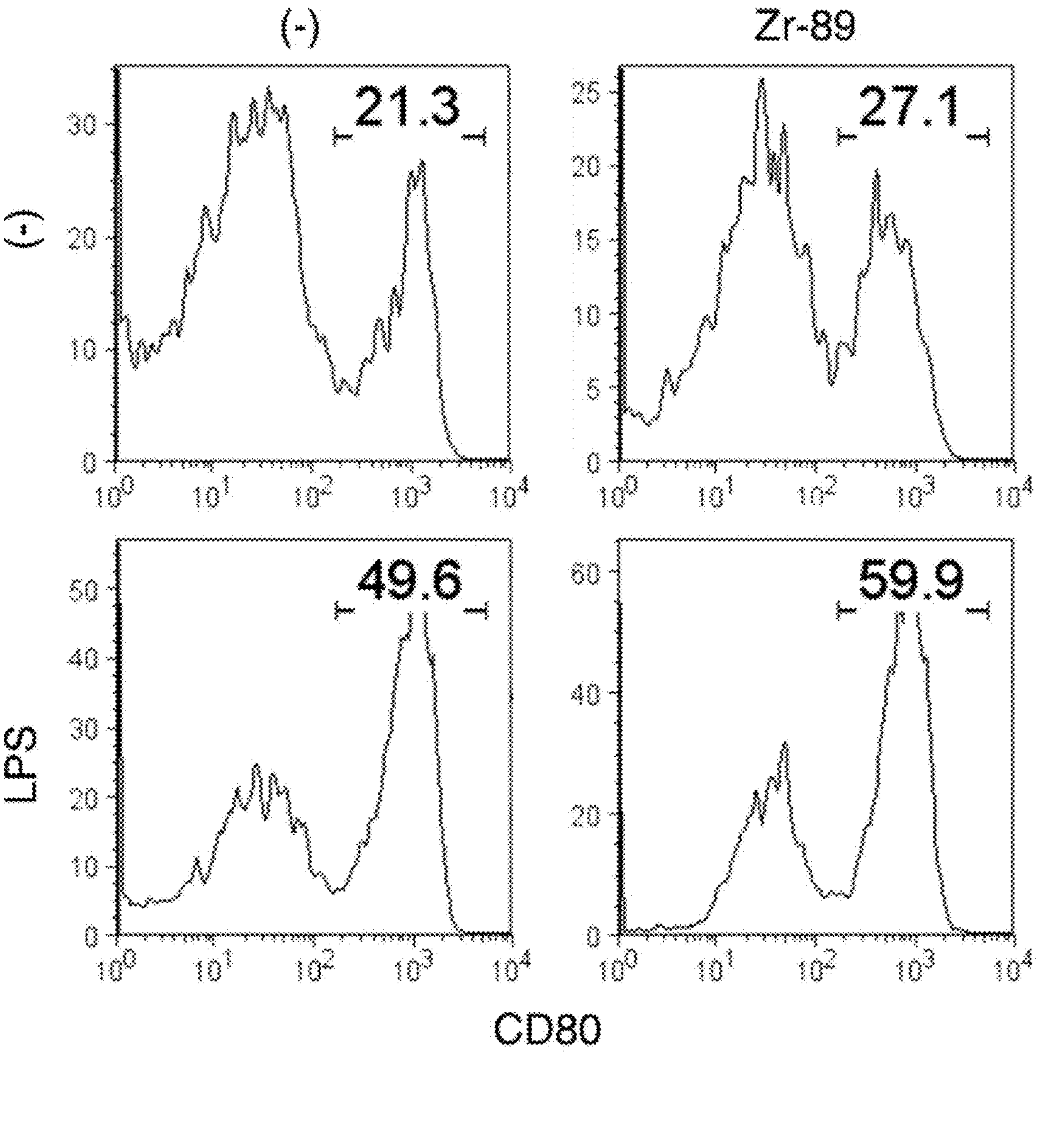
FIGS. 3A-3E shows that $^{89}$Zr-oxine complex-labeled DCs upregulated CD80 (FIG. 3A), CD86 (FIG. 3B), and CD40 (FIG. 3C), as well as MHC molecules of class I (FIG. 3D) and class II (FIG. 3E) similarly to non-labeled control DCs when DCs were activated by a Toll-like receptor ligands, lipopolysaccharide (LPS).
Figure 3B:
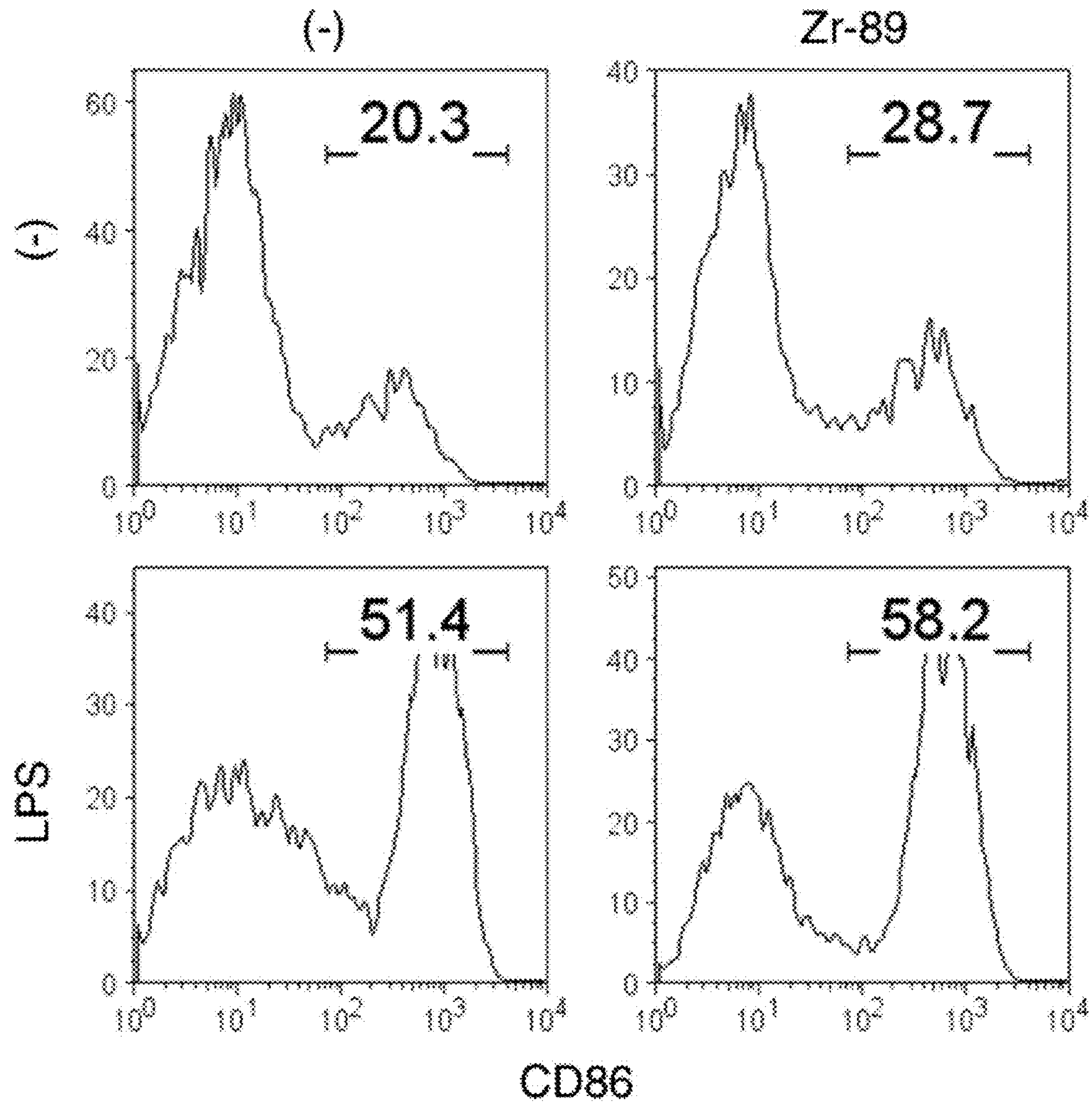
Figure 3C:
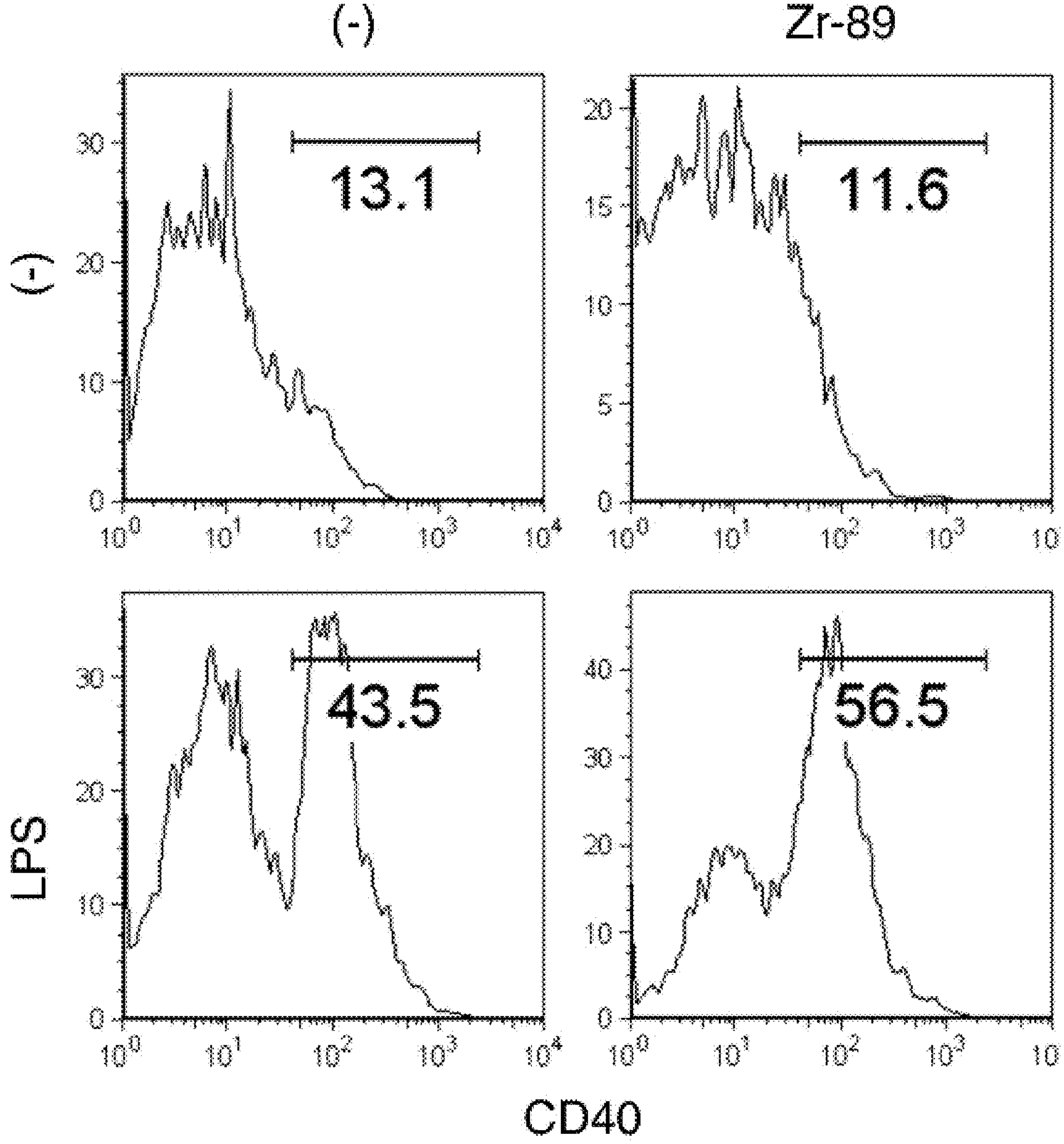
Figure 3D:
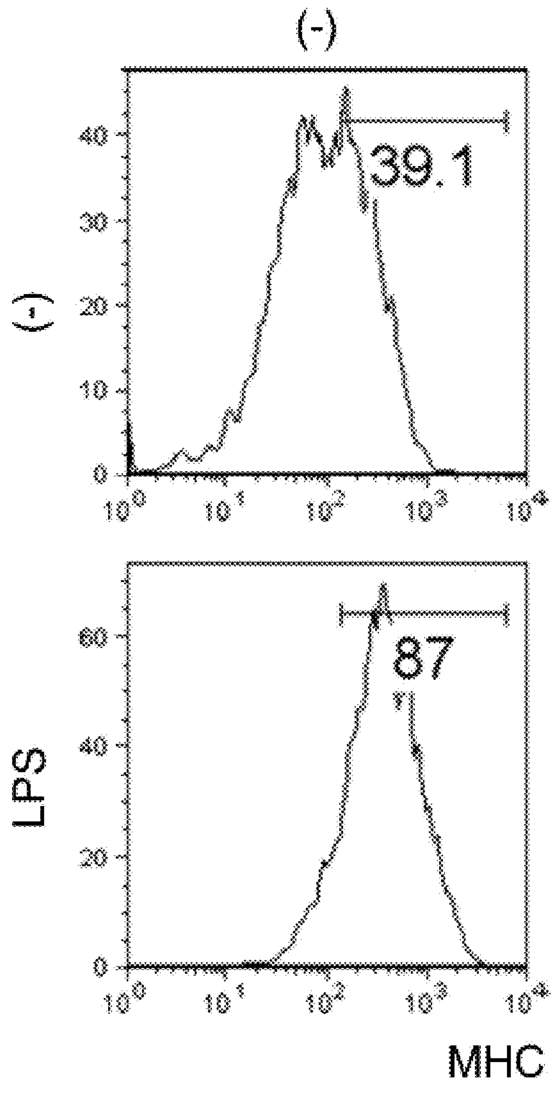
Figure 3E:
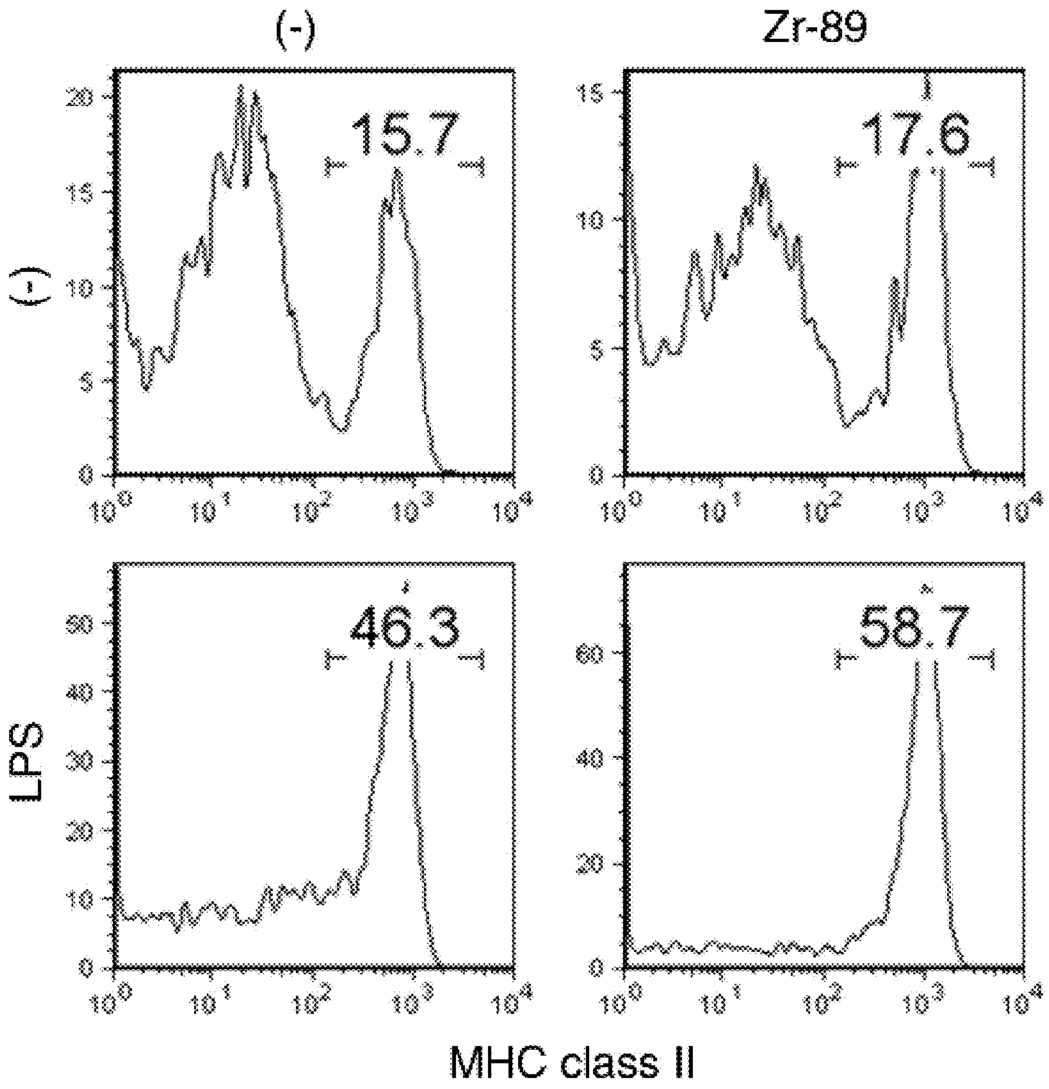
Figure 3F:
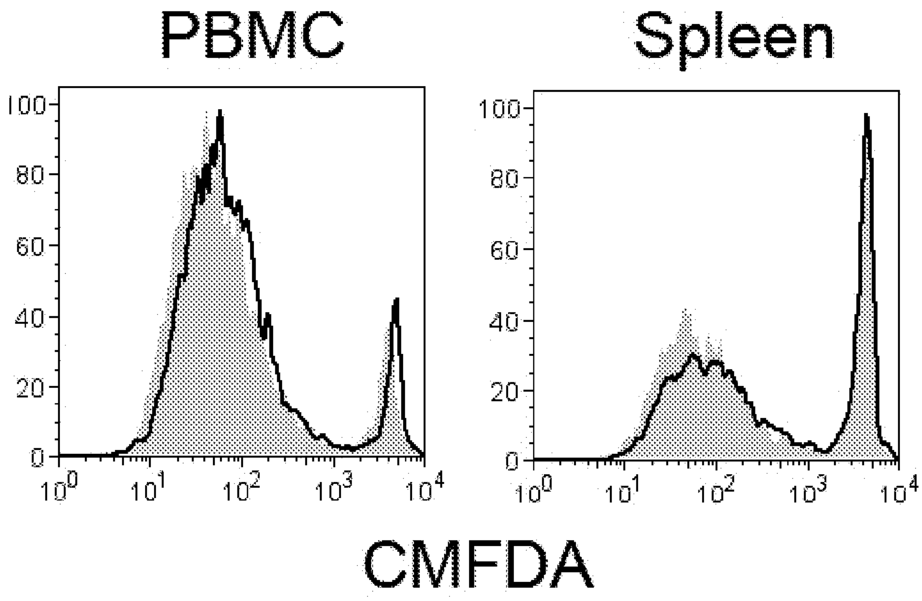
FIG. 3F shows that $^{89}$Zr-oxine complex-labeled DCs were capable of presenting the antigen and inducing T cell activation in vivo as well as non-labeled DCs.

In order to determine the effect of $^{89}$Zr-oxine complex on the functionality of DCs and CTLs, labeled DCs were activated by LPS and labeled CTLs were activated through TCR. $^{89}$Zr-oxine complex labeling resulted in slightly increased expression of B7 molecules, CD80 and CD86, on DCs prior to LPS activation. After overnight stimulation with LPS, $^{89}$Zr-oxine labeled DCs upregulated CD80, CD86, and CD40, as well as MHC molecules (FIGS. 3A-E), similar to non-labeled control DCs. To confirm that the labeled DCs were still capable of presenting antigens to T cells, $^{89}$Zr-oxine labeled DCs were stimulated with LPS together with ovalbumin peptide (OVA), and injected into mice transferred with CMFDA labeled OT-1 CD8 T cells expressing TCR against OVA 1 day before DC administration. Flow cytometry analysis of OT-1 T cells collected from the spleen and blood 4 days after the DC transfer demonstrated that $^{89}$Zr-oxine-labeled DCs (black line) were capable of presenting the antigen and inducing T cell activation and proliferation as well as non-labeled DCs (gray shadow) (FIG. 3F).

Figure 4A:
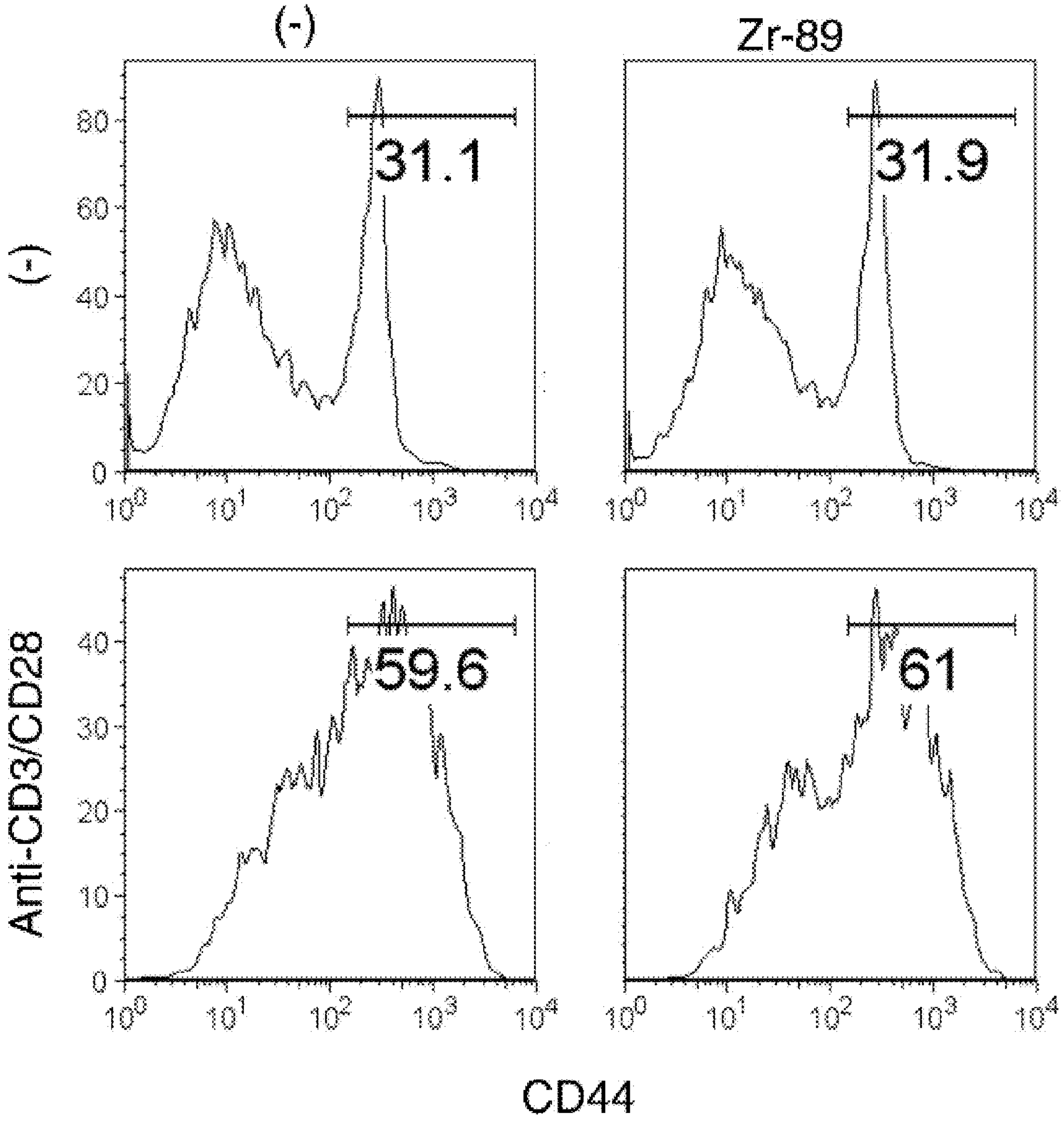
FIGS. 4A-4C shows that $^{89}$Zr-oxine complex-labeled CTLs were activated upon TCR stimulation as well as non-labeled cells as indicated by induction of CD44 (FIG. 4A), CD69 (FIG. 4B), and CD25 expression (FIG. 4C).
Figure 4B:
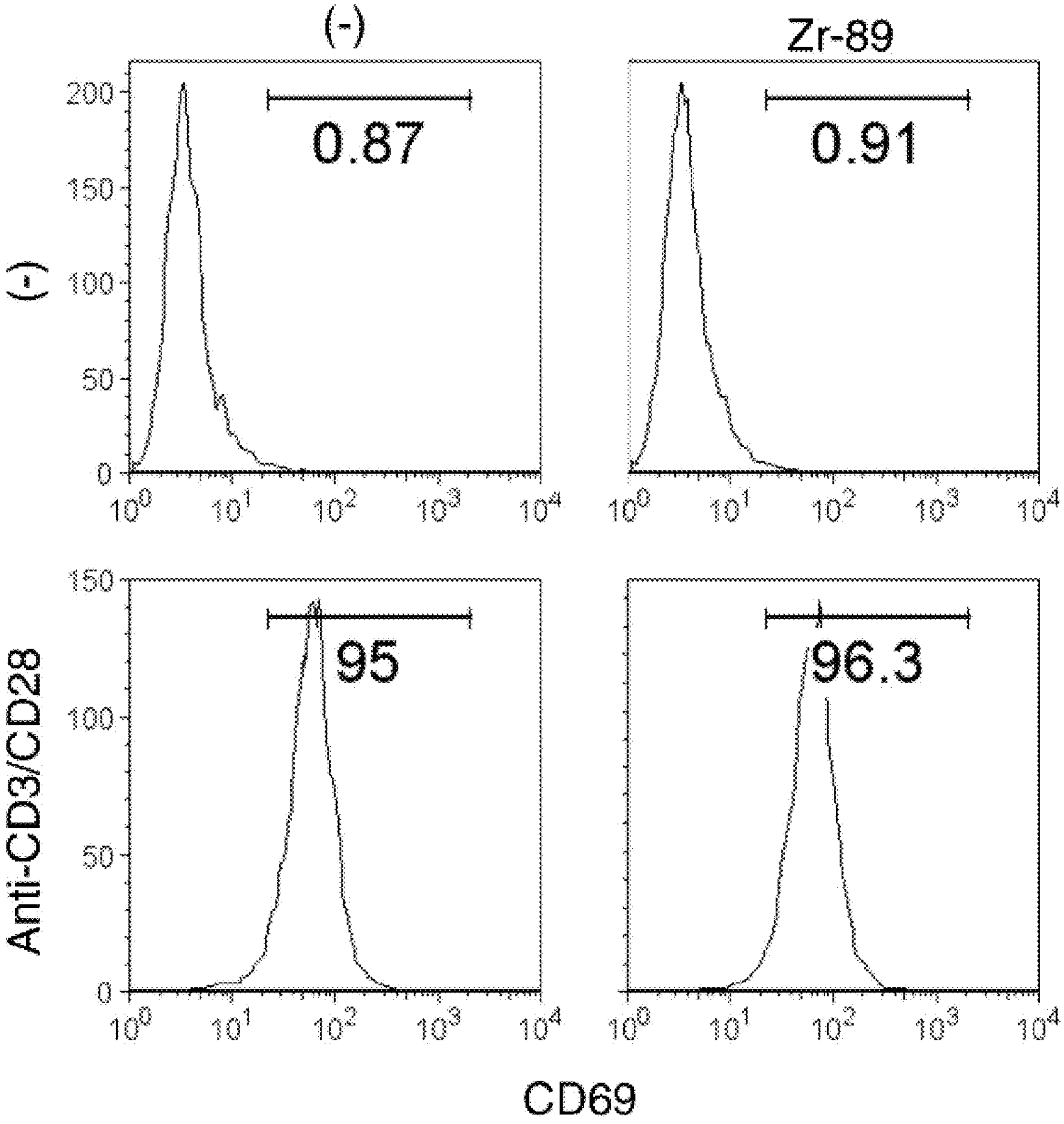
Figure 4C:
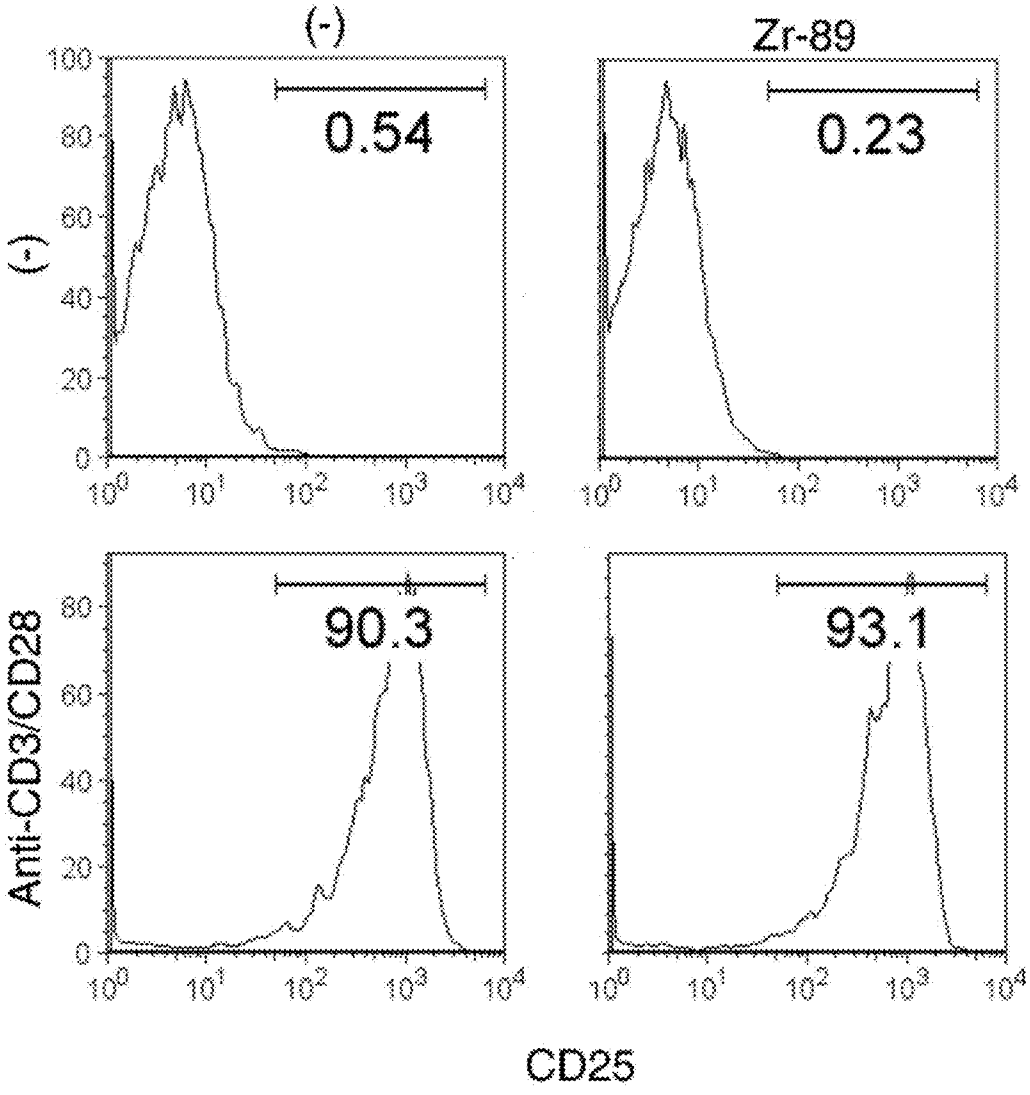
Figure 4D:
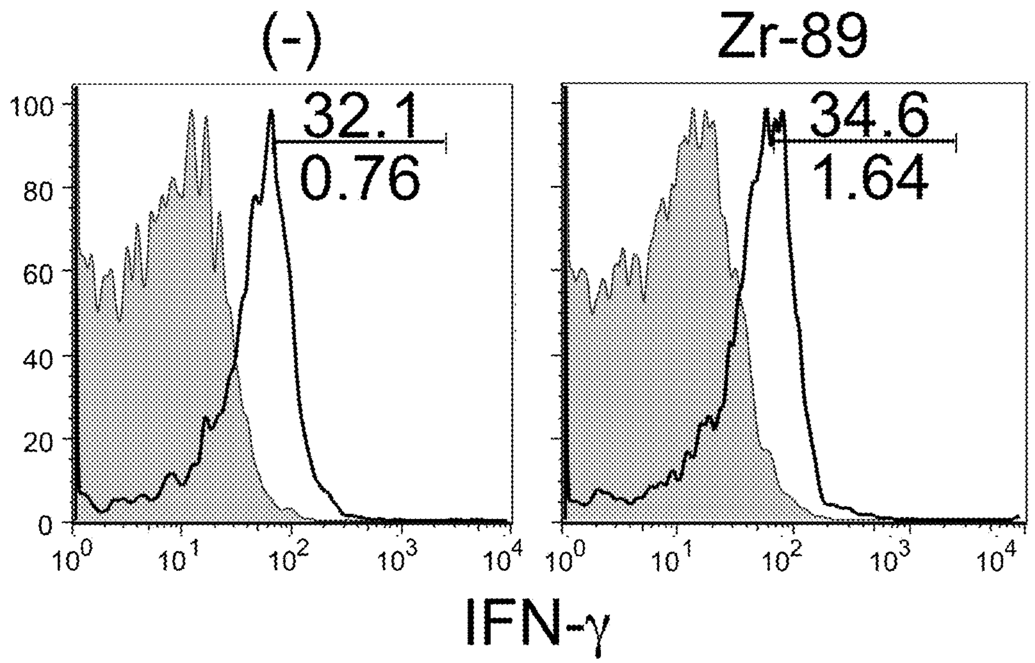
FIGS. 4D-4E shows that the $^{89}$Zr-oxine complex-labeled CTLs were capable of producing IFN-γ (FIG. 4D) and IL-2 (FIG. 4E) upon TCR activation.
Figure 4E:
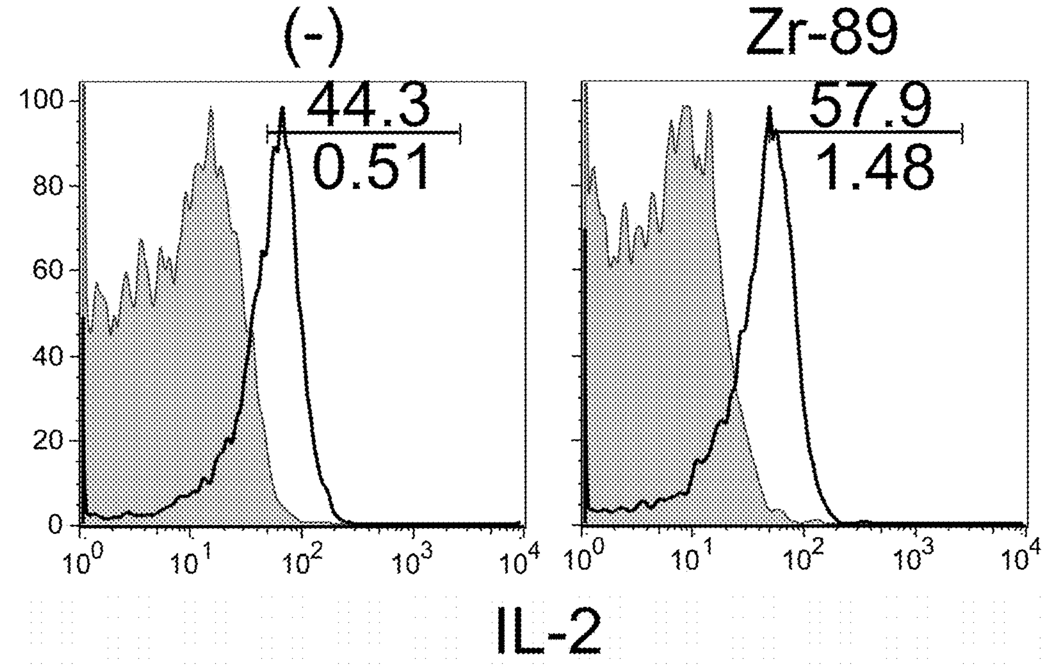

CTLs were TCR stimulated after the $^{89}$Zr-oxine complex labeling. TCR stimulation induced upregulation of CD69, CD25 and CD44 markers in the labeled and non labeled CTLs at the similar levels (FIGS. 4A-4C). The labeling did not negatively affect the production of interferon gamma (IFNγ) and Interleukin 2 (IL-2) (FIGS. 4D and 4E), suggesting that the cytotoxic functions of CTLs were maintained after labeling.

EXAMPLE 7

This example demonstrates that $^{89}$Zr-oxine complex labeling of transferred DCs and CTLs enabled visualization on microPET.

Figure 5A:
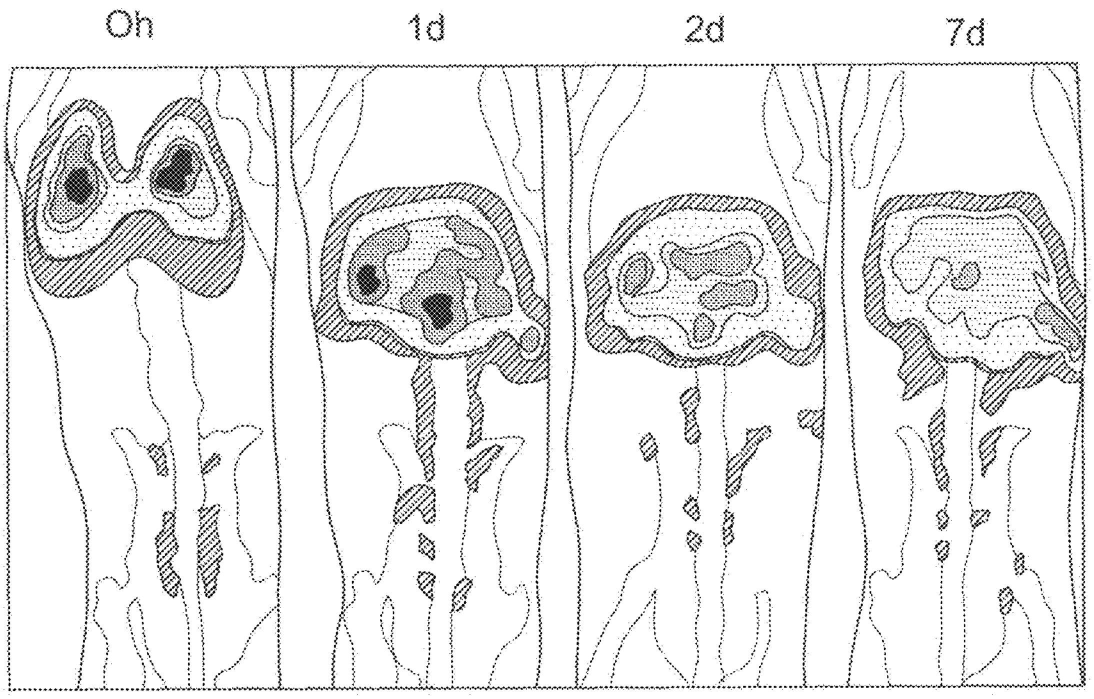
FIG. 5A shows that $^{89}$Zr-oxine complex-labeled DCs injected into mice via the tail vein initially distributed in the lungs and gradually migrated to the spleen and liver by day 1, detected by microPET imaging.
Figure 7A:
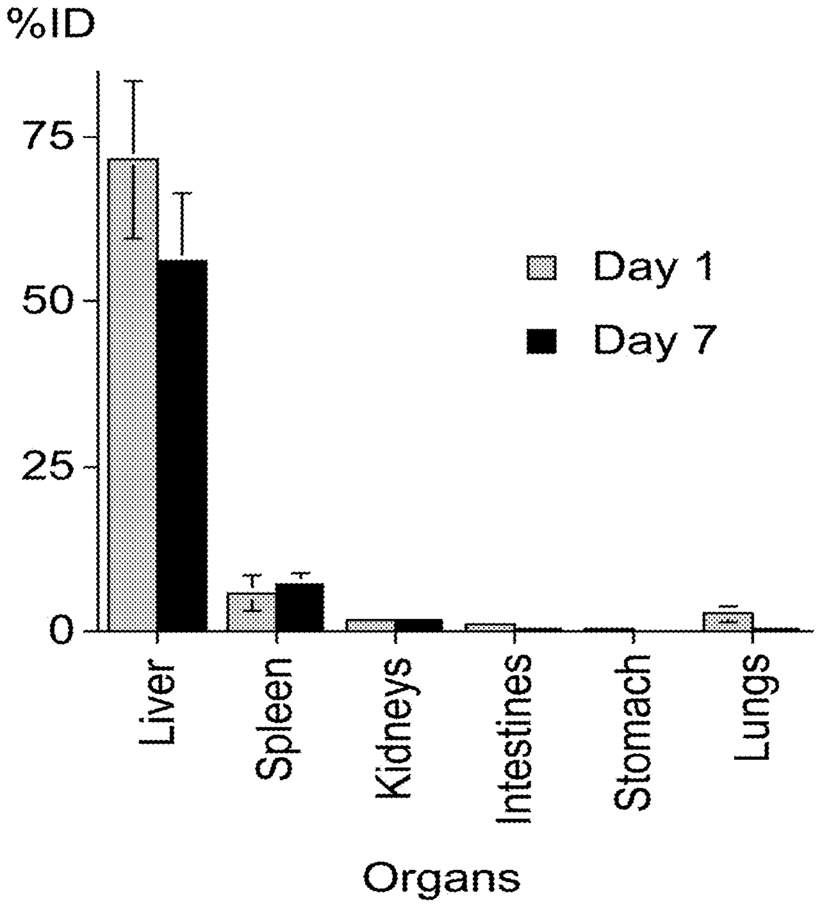
FIGS. 7A and 7B illustrate the biodistribution of $^{89}$Zr-oxine complex-labeled DCs at 1 and 7 days, respectively, after the transfer to WT mice.
Figure 7B:
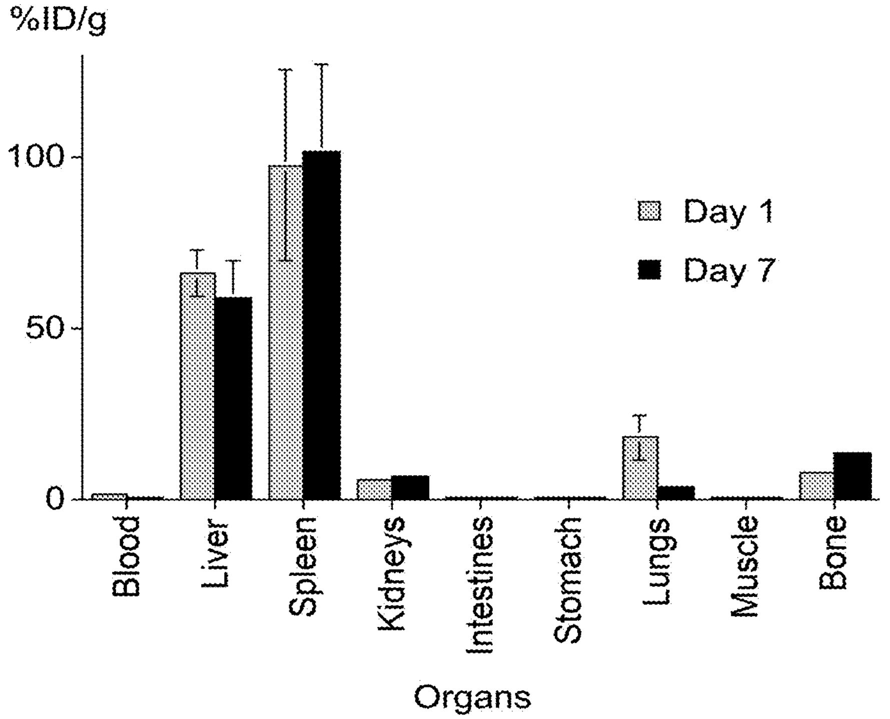

DCs labeled with $^{89}$Zr-oxine complex were visualized in vivo with microPET imaging (FIG. 5A). Labeled DCs injected via the tail vein (444 kBq or 12 μCi/5 million cells) initially distributed in the lungs, and gradually migrated to the spleen and liver by day 1 (FIG. 5A). The DCs remained in the liver and spleen during the 7 day-imaging period. This distribution was confirmed by a biodistribution study analyzing the radioactivity of each organ harvested from the mice on day 1 and day 7 (FIG. 7). The low activity shown in the kidneys and the bone (femur) was likely due to free $^{89}$Zr released from dead cells.

Figure 5B:
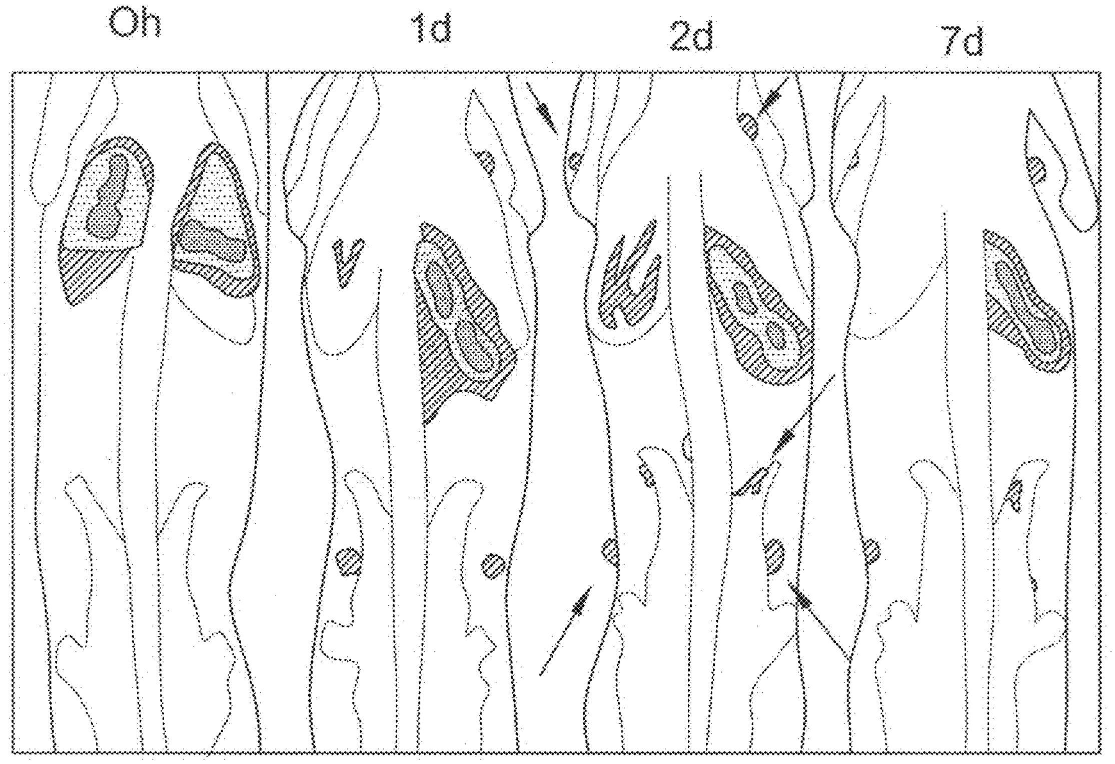
FIG. 5B shows that CTLs labeled with $^{89}$Zr-oxine complex mainly distributed in the spleen after migrating out from the lungs after injection into mice via the tail vein, detected by microPET imaging.

CTLs purified from the spleen of WT mice and labeled with $^{89}$Zr-oxine complex labeling (185 kBq or 5 μCi/5 million cells) were tracked over 7 days. Unlike DCs, CTLs mainly distributed in the spleen and lymph nodes after migrating out from the lungs (FIG. 5B). Arrows indicate examples of lymph node accumulation of CTLcytotoxic T cells.

EXAMPLE 8

This example demonstrates that $^{89}$Zr-oxine complex-labeled CTLs targeted tumor.

Figure 6A:
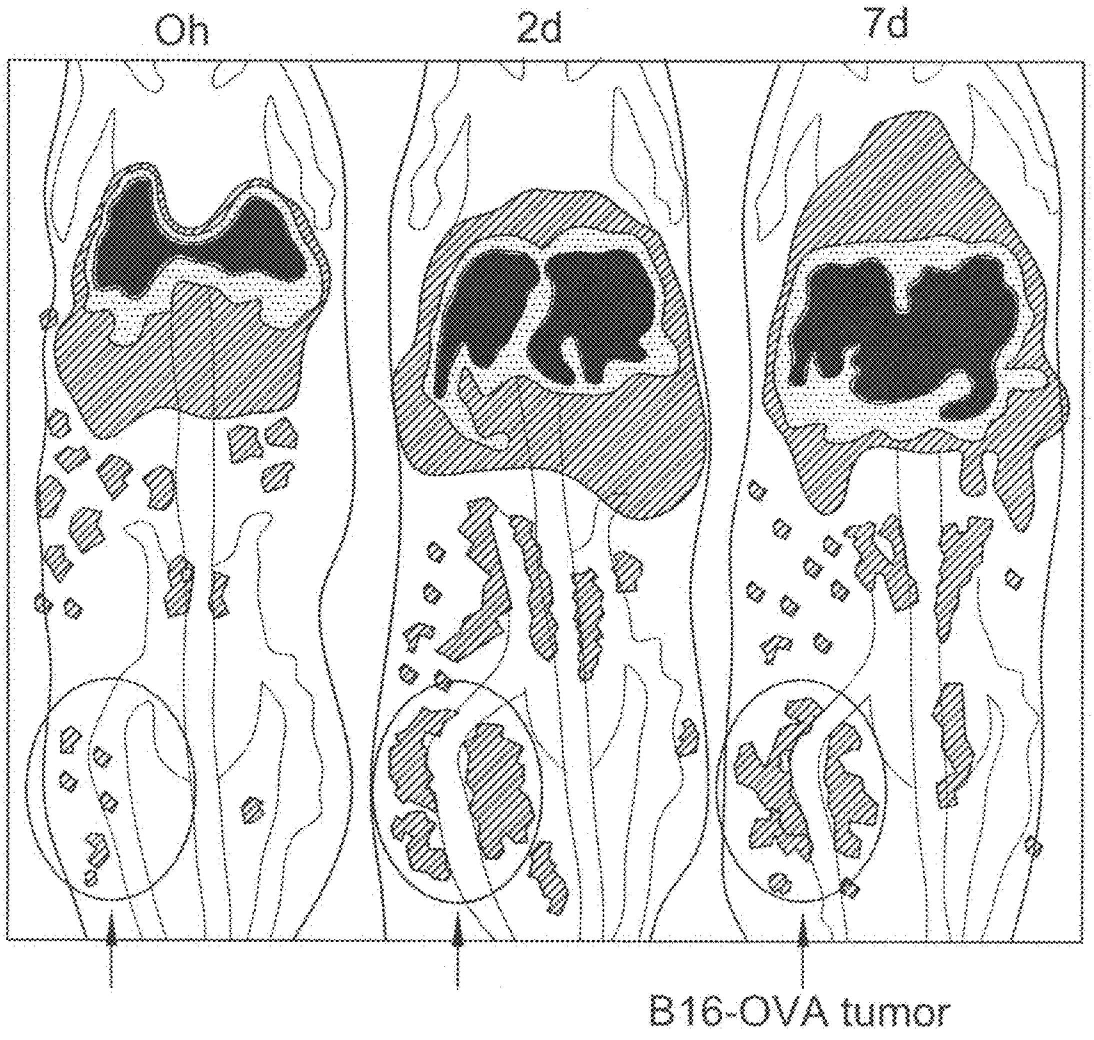
FIG. 6A depicts microPET imaging of $^{89}$Zr-oxine complex labeled OT-1 TCR transgenic CTLs targeting melanoma tumors expressing the nominal antigen inoculated in the flank.
Figure 6B:
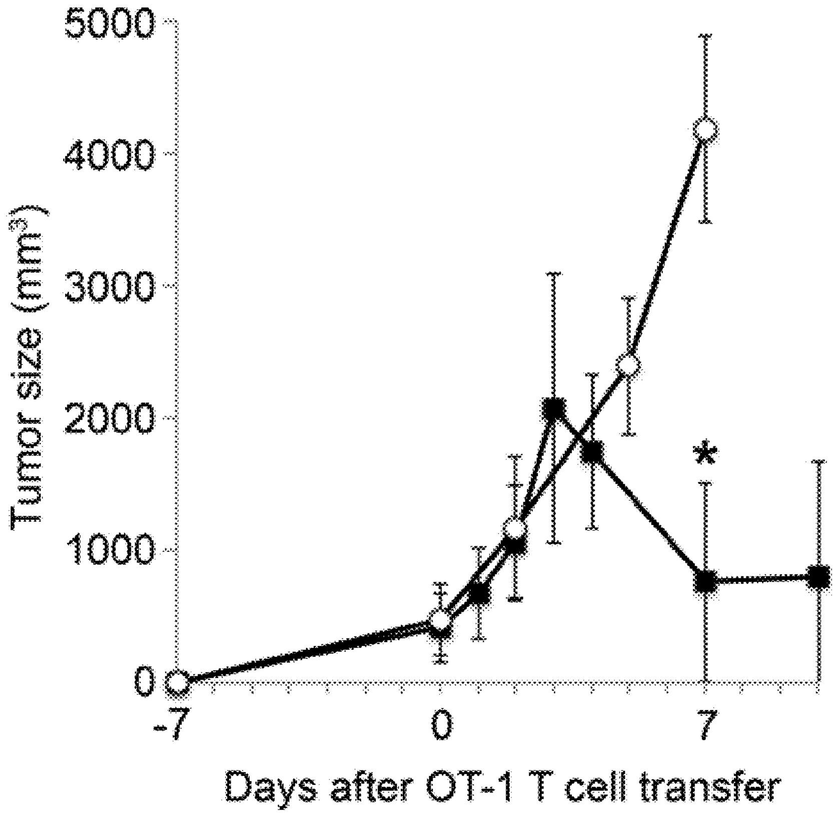
FIG. 6B shows that the $^{89}$Zr-oxine complex labeled OT-1 CTLs (■) retained cytotoxic function and induced regression of melanoma tumors expressing the nominal antigen after the transfer compared to untreated subjects (○).

The tumor targeting properties of $^{89}$Zr-oxine complex-labeled CTLs were examined using ex vivo activated OT-1 CD8 T cells in a B16 melanoma xenograft model. Rag1KO mice bearing B16 tumor expressing OVA (B16-OVA, ~1 cm diameter) were injected with one million splenocytes of WT mice 6 hours before the OT-1 T cell transfer. The $^{89}$Zr-oxine complex-labeled OT-1 T cells (248.5 kBq or 6.7 μCi/7.7 million cells) were adoptively transferred and serial imaging was performed. FIG. 6A shows the migration of OT-1 T cells to the tumor, which accumulated over time. The B16-OVA tumor underwent regression after the $^{89}$Zr-oxine complex-labeled OT-1 T transfer, indicating that cytotoxic action of CTLs was maintained after $^{89}$Zr-oxine complex labeling, leading to a dramatic response in the tumor (FIG. 6B). Untreated mice were sacrificed on day 7, as the tumor diameter reached 20 mm (n=5). *P=2.84×10-5 on day 7 according to Holm-Sidak multiple tests that included three tests corresponding to days 2, 5, and 7 (FIG. 6B). Error bars indicate standard deviations.

EXAMPLE 9

This example demonstrates $^{89}$Zr-oxine bone marrow (BM) cell labeling and the determination of cell viability and cellular retention of $^{89}$Zr.

BM cells were incubated with 11.0-55.5 kBq/$10^6$ cells of $^{89}$Zr-oxine complex in PBS at 25:1 volume ratios for 20 minutes, washed twice in RPMI media and transferred to a new tube. The cell-associated radioactivity was 3.0-16.7 kBq, yielding the labeling efficiency of 24-30%. To determine cell viability and retention of $^{89}$Zr after the labeling, BM cells were labeled with 2 different radioactivity doses, 28.12 kBq/$10^6$ and 8.14 kBq/$10^6$ cells, and cultured with SCF, FLT3L and TPO (100 ng/ml each). The number of live cells was counted using 0.4% trypan blue dye (Life Technologies) at 0 h, 2 d, 4 d, and 7 d (n=3). At each time point, the cell suspension was spun to separate the supernatant and the cell pellet, and the radioactivity of both fractions was measured by a γ-counter (WIZARD$^2$ automatic gamma-counter, Perkin Elmer, Waltham, MA).

The culture with combination of SCF, FLT3L and TPO sustained the survival of a fraction of BM cells as indicated in FIG. 8A. $^{89}$Zr-labeling at 8.14 kBq/$10^6$ cells showed slight proliferation after day 4, whereas cells labeled at 28.12 kBq/$10^6$ cells slightly decreased in number. With the lower labeling dose, the suppression of the proliferation was limited to approximately 50% (global P=0.0417 against non-labeled control). The total $^{89}$Zr activities associated with the cells declined as the cells not responding to the cytokines died during the initial 0-2 day period, but plateaued thereafter (FIG. 8B; global P=0.25). As the cells labeled with the lower dose started to proliferate, the specific activity declined, but specific activity for the cells labeled with the higher dose remained about the same as they failed to proliferate (FIG. 8C; global P=0.25).

EXAMPLE 10

This example demonstrates the determination of the effects of labeling on the phenotype of BM cells and differentiation capability in vitro.

The surface expressions of CD117, sca-1 and lineage markers (CD3, NK1.1, Ly6G, CD2, CD5 and B220) on BM cells were examined before and after $^{89}$Zr-oxine labeling (3.15 kBq/2×$10^6$) and analyzed by flow cytometry using a FACS Calibur flow cytometer (Becton Dickinson, San Jose, CA) and analyzed using FlowJo software (Tree Star, Inc., Ashland, OR). BM cell differentiation capability was examined by culturing the $^{89}$Zr-labeled and non-labeled cells with GM-CSF (20 ng/ml) and IL-15 (25 nM) for differentiation to DCs and NK/NK-T cells (n=3). On day 10, the cells were harvested, stained with anti-CD11c, CD86, and NK1.1 antibodies, and analyzed on flow cytometry. For the GM-CSF culture, cell associated-$^{89}$Zr activity and cell number were also examined.

$^{89}$Zr-oxine labeled cells expressed CD117, sca-1 and lineage markers (CD3, NK1.1, Ly6G, CD2, CD5 and B220) at similar levels to non-labeled controls (FIG. 9A). CD117$^+$ sca-1$^+$HSCs were 4.7-4.8% of lineage negative cells, and slightly more than 0.4% of the total BM cells. GM-CSF culture of BM Cells, labeled at 39.3 and 26.9 kBq/$10^6$ cells, demonstrated similar survival and minimal suppression of proliferation in comparison to non-labeled controls during the differentiation into DCs. Because most BM cells were non-responders to GM-CSF and died, retention of $^{89}$Zr in whole culture rapidly decreased during the initial 3 day-period and remained low thereafter. After a 10 day-culture with GM-CSF, the BM cells labeled with $^{89}$Zr-oxine differentiated to CD11c$^+$ DCs with about half of the cells expressing CD86, indicating that they are mature DCs (FIG. 9B). When IL-15 was used, cells became NK1.1$^+$ cells, suggesting their differentiation into NK'NK-T cells (FIG. 9C). These results indicated that $^{89}$Zr-oxine labeled cells retained the capacity to proliferate and differentiate normally into mature cells in vitro.

EXAMPLE 11

This example demonstrates BM cell tracking by micro-PET/CT.

$^{89}$Zr-oxine labeled BM cells were transferred to mice i.v. at 331 kBq/2×$10^7$ cells. For BM ablation, host mice received a 9.5 Gy lethal whole-body irradiation 24 h prior to cell transfer (n=5). In addition, mice received deferoxamine, a chelator, (Hospira, Inc., Lake Forest, IL) at 660 μg intramuscularly 15 min before and 1, 2, 3 and 4 hr after the cell injection to hasten the renal excretion of free $^{89}$Zr released from cells that died after the transfer. Imaging was performed using a microPET/CT imager (BioPET, Bioscan, Washington, DC) up to 7 days (Suppl. Methods). InVivo Quant software (inviCRO LLC, Boston, MA) was used to fuse the maximum intensity projection PET images with CT images and to quantify cells migrated to various organs by setting volumes of interest on the acquired images.

It was observed that the donor cells quickly passed through the lungs, with a small fraction of cells migrating to the BM, spleen and liver almost immediately following the transfer (FIGS. 10A and 10B). The majority of donor cells rapidly left the lungs within 4 h and migrated to the BM and spleen and remained in these organs until day 7. BM ablation prior to the cell transfer was performed in some animals (n=3). Subsequent PET/CT imaging showed no clear difference in the initial migration of the donor cells to the BM comparing BM ablated and non-ablated mice and trafficking pattern of the two groups remained similar up to day 7 (FIG. 10A). The analysis of cell migration kinetics to the BM, spleen and liver in both groups were also similar (n=3, FIG. 10B). It was calculated that when 2×$10^7$ cells were transferred, approximately $4.4\times10^6$ cells homed to the BM and $2.3\times10^6$ and $7.1\times10^6$ cells to the spleen and liver, respectively, by 4 h (FIG. 10B).

EXAMPLE 12

This example demonstrates role of CXCR4 in the BM cell trafficking.

A CXCR4 inhibitor, plerixafor (Adooq Bioscience, Irvine, CA), was used to interrogate the role of CXCR4 in BM cell migration (n=4). Mice received an i.v. injection of plerixafor (5 mg/kg) 15 min before and 1 day after the $^{89}$Zr-oxine labeled BM cell transfer (331 kBq/$2\times10^7$ cells). Another group of mice received concurrent i.v. injections of G-CSF (2.5 μg, n=4). Deferoxamine was injected intramuscularly 15 min before and 1, 2, 3 and 4 hr after the cell injection. Serial microPET/CT images were acquired.

Inhibition of CXCR4 by plerixafor significantly inhibited the migration of labeled cells to the BM at 2 h (FIGS. 11A and 11B) indicating that CXCR4 signaling is critical for BM homing. This blockade of the initial BM homing lasted even longer when G-CSF was additionally administered (FIGS. 11A and B). Based on the trafficking kinetics analyzed from the PET images, approximately $4.9\times10^5$ cells were mobilized by plerixafor injected on day 1, suggesting that their retention in the BM also depended on CXCR4-CXCL12 system (FIG. 11B). Similarly, the combination of plerixafor/G-CSF mobilized approximately $1.04\times10^5$ cells on day 1, which indicated that even the donor cells homed to the BM by day 1 under the plerixafor/G-CSF treatment was low, yet further treatment still forced the BM cells to mobilize out of the BM.

EXAMPLE 13

This example demonstrates the quantification of BM cell mobilization.

BM cells collected from GFP transgenic mice (222 kBq/$2\times10^7$ cells) were labeled with $^{89}$Zr-oxine and transferred to wild type mice (n=4). Mice received i.v. injections of plerixafor and G-CSF 3 h and 1 day following the cell transfer. Two hours after the second mobilization treatment, mice were sacrificed by $CO_2$ asphyxiation and the blood was collected by a cardiac puncture into EDTA-coated tubes (BIOTANG Inc., Lexington, MA). The volume was measured, then the blood was spun and the radioactivity of the cell fraction was measured by a γ-counter. Radioactivity of the total blood was calculated using the following formula using the 1.1 ml average blood volume for a 20-g mice; (Circulating $^{89}$Zr-labeled BM cells)=(Total injected cell number)×(radioactivity of the blood sample)/(Total injected radioactivity)×1.1 (ml)/(sample blood volume [ml])×body weight (g)/20. The collected blood cells were also analyzed by flow cytometry.

The strong effect of plerixafor and G-CSF in inhibiting BM homing and further inducing mobilization of BM cells prompted quantification of the mobilization effect of plerixafor/G-CSF on pre-transplanted BM cells. The injection of plerixafor/G-CSF on two consecutive days induced a 3.5-fold increase of $^{89}$Zr activity in the circulation in mice pre-transplanted with $^{89}$Zr-labeled BM cells (FIG. 12A; P=0.0192), corresponding to an increase from $0.31\times10^5$ cells to $1.1\times10^5$ cells in the circulation by the mobilization. The cell number calculated from the blood radioactivity was consistent with what was estimated from the PET image-quantification above. Because the $^{89}$Zr-labeled cells in the spine were about $4.4\times10^6$, approximately 2% of the BM cells were mobilized by the 2 doses of plerixafor/G-CSF treatment. Flow cytometry analyses confirmed an increase of GFP$^+$ cells in the blood in mice treated with plerixafor/G-CSF compared to controls (FIG. 12B).

EXAMPLE 14

This example demonstrates the flow cytometry analysis for engraftment of $^{89}$Zr-oxine labeled BM cells and differentiation in vivo.

The engraftment and differentiation of the $^{89}$Zr-oxine labeled BM cells was examined by transferring CD45.1 expressing donor cells to CD45.2 expressing hosts or vice versa (n=3). Ten-weeks later, the BM cells and splenocytes collected from the recipient mice were stained with antibodies against CD45.1 and CD45.2 congenic markers. Splenocytes were also stained with antibodies against CD3, CD4, CD8, NK1.1, and CD11c. Cells were analyzed by flow cytometry.

Flow cytometry analysis of recipient BM revealed that $^{89}$Zr-labeled donor cells had engrafted only when the host mice had received whole-body irradiation before the BM transfer (FIGS. 13A and 13B) In the BM ablated mice, 79% of BM cells were $^{89}$Zr-labeled donor cell origin (FIG. 13Ai) and phenotypically similar to the control mice that received unlabeled BM cells. In the periphery, about 90% of splenocytes consisted of donor-derived cells (FIG. 13Bi), which included mature DCs (CD11c$^+$, FIG. 13Bii), and T cells (CD3$^+$NK1.1$^-$, FIG. 13Biii), and NK cells (CD3$^-$NK1.1$^+$, FIG. 13Biv). These results suggest that critical functions of BM cells, such as homing capacity to the BM, engraftment in the BM niche, and differentiation into mature cells, were retained in $^{89}$Zr-oxine labeled cells.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments can become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A kit for labeling a protein of a biological cell comprising (a) a first component comprising a solution of $^{89}ZrCl_4$ in hydrochloric acid, (b) a second component comprising oxine and hydrochloric acid, (c) an alkaline solution comprising a base sodium bicarbonate in an amount effective to neutralize a mixture of components (a) and (b), (d) a nonionic surfactant, which is polysorbate 80; and (e) instructions for preparing a labeling agent by utilizing (a), (b), (c), and (d);

wherein the kit further includes instructions to carry out labeling of the biological cell at a temperature of 16 to 26° C.

2. The kit of claim 1, wherein the first component is in a first container, and the second component is in a second container.

3. The kit of claim 2, wherein the alkaline solution is in a third container.

4. The kit of claim 1 further comprising at least one other labeling agent.

5. The kit of claim 4, wherein the at least one other labeling agent is selected from the group consisting of a superparamagnetic nanoparticle, $^{19}F$, an optical dye, and a combination thereof.

6. The kit of claim 1, wherein the biological cell is a natural killer (NK) cell.

7. The kit of claim 1, wherein the biological cell is selected from the group consisting of a T cell, a natural killer (NK) cell, a dendritic cell, a macrophage, a monocyte, a B cell, a myeloid cell, a platelet, a stem cell, a progenitor cell, a mesenchymal cell, an epithelial cell, a neural cell, a skeletal myoblast, and a pancreatic islet cell.

8. The kit of claim 1, wherein $^{89}ZrCl_4$ is present as a solution in 1M hydrochloric acid.

9. The kit of claim 1, wherein the alkaline solution is a 0.5M solution.

* * * * *